US010925943B2

(12) United States Patent
Pulé et al.

(10) Patent No.: US 10,925,943 B2
(45) Date of Patent: Feb. 23, 2021

(54) MARKER-SUICIDE GENE USEFUL IN ADOPTIVE CELL THERAPY

(71) Applicant: UCL BUSINESS LTD, London (GB)

(72) Inventors: Martin Pulé, London (GB); Brian Philip, London (GB)

(73) Assignee: UCL BUSINESS LTD, London (GB)

( * ) Notice: Subject to any disclaimer, the term of this patent is extended or adjusted under 35 U.S.C. 154(b) by 477 days.

(21) Appl. No.: 14/391,536

(22) PCT Filed: Apr. 11, 2013

(86) PCT No.: PCT/GB2013/050935
§ 371 (c)(1),
(2) Date: Oct. 9, 2014

(87) PCT Pub. No.: WO2013/153391
PCT Pub. Date: Oct. 17, 2013

(65) Prior Publication Data

US 2015/0093401 A1 Apr. 2, 2015

(30) Foreign Application Priority Data

Apr. 13, 2012 (GB) ..................................... 1206559

(51) Int. Cl.

| | |
|---|---|
| ***A61K 39/00*** | (2006.01) |
| ***G01N 33/50*** | (2006.01) |
| ***A61K 35/14*** | (2015.01) |
| ***C07K 14/705*** | (2006.01) |
| ***C07K 16/28*** | (2006.01) |
| ***A61K 35/17*** | (2015.01) |
| ***C07K 14/725*** | (2006.01) |
| ***C12N 15/85*** | (2006.01) |
| *A61K 48/00* | (2006.01) |

(52) U.S. Cl.
CPC .......... *A61K 39/0011* (2013.01); *A61K 35/17* (2013.01); *C07K 14/7051* (2013.01); *C07K 14/70503* (2013.01); *C07K 14/70517* (2013.01); *C07K 14/70596* (2013.01); *C07K 16/2887* (2013.01); *C07K 16/2896* (2013.01); *C12N 15/85* (2013.01); *G01N 33/5005* (2013.01); *A61K 48/00* (2013.01); *A61K 2039/5158* (2013.01); *A61K 2039/572* (2013.01); *A61K 2039/585* (2013.01); *C07K 2317/34* (2013.01); *C07K 2317/52* (2013.01); *C07K 2319/03* (2013.01); *C07K 2319/33* (2013.01); *C07K 2319/40* (2013.01); *C07K 2319/60* (2013.01); *C07K 2319/70* (2013.01)

(58) Field of Classification Search
None
See application file for complete search history.

(56) References Cited

U.S. PATENT DOCUMENTS

2017/0066838 A1 3/2017 Pule et al.

FOREIGN PATENT DOCUMENTS

| | | |
|---|---|---|
| CN | 101687015 A | 3/2010 |
| WO | WO-2008/076437 A2 | 6/2008 |
| WO | WO-2008/087541 A1 | 7/2008 |

OTHER PUBLICATIONS

Philip et al. (Blood 2014, vol. 124 No. 8 pp. 1277-1287 and Supplemental Data).*
Blood Editorial Policies [Retrieved on Jul. 20, 2020 from the Internet: https://ashpublications.org/blood/pages/editorial_policies].*
Bendle et al., Lethal graft-versus-host disease in mouse models of T cell receptor gene therapy, Nature Medicine, 16(5):565-571 (May 2010).
Branchini et al., Red-emitting luciferases for bioluminescence report and imaging applications, Analytical Biochemistry, 396: 290-7 (2010).
Brentjens et al., Treatment of Chronic Lymphocytic Leukemia with Genetically Targeted Autologous T Cells: Case report of an Unforeseen Adverse Event in a Phase I Clinical Trial, Molecular Therapy, 18(4):666-8 (2010).
Brewin et al., Generation of EBV-specific cytotoxic T cells that are resistant to calcineurin inhibitors for the treatment of posttransplantation lymphoproliferative disease, Blood, 114(23):4792-803 (2009).
Donnelly et al., "The 'cleavage' activities of foot-and-mouth disease virus 2A site-directed mutants and naturally occurring '2A-like' sequences", J. Gen. Virol. 82(5):1027-1041 (2001).
Hu et al., A dicistronic retroviral vector encoding HSV TK and CD20 for positive selection and conditional ablation of human T cells, Blood, 96(11):380b (2000).
Kochenderfer et al., Eradication of B-lineage cells and regression of lymphoma in a patient treated with autologous T cells genetically engineered to recognize CD19, Blood, 116(20):4099-102 (2010).
Kohn et al., CARs on track in the clinic, Mol. Ther., 19(3):432-8 (2011).

(Continued)

*Primary Examiner* — Sharon X Wen
(74) *Attorney, Agent, or Firm* — Marshall, Gerstein & Borun LLP

(57) ABSTRACT

The present invention provides a polypeptide having the formula: St-R1-S1-Q-S2-R2 wherein St is a stalk sequence which, when the polypeptide is expressed at the surface of a target cell, causes the R and Q epitopes to be projected from the cell surface; R1 and R2 are a Rituximab-binding epitopes each having the an amino acid sequence selected from the group consisting of SEQ ID No. 1, 6, 7, 8, 9, 10, 11, 12, 13, 14, 15 and 16 or a variant thereof which retains Rituximab-binding activity; S1 and S2 are optional spacer sequences, which may be the same or different; and Q is a QBEnd1O-binding epitope having the amino acid sequence shown as SEQ ID No. 2 or a variant thereof which QBEnd1O-binding activity. The invention also provides a nucleic acid sequence encoding such a polypeptide and uses thereof in adoptive cell transfer.

12 Claims, 15 Drawing Sheets

Specification includes a Sequence Listing.

(56) References Cited

OTHER PUBLICATIONS

Lamers et al., Treatment of Metastatic Renal Cell Carcinoma with Autologous T-Lymphocytes Genetically Retargeted Against Carbonic Anhydrase IX: First Clinical Experience, Journal of Clinical Oncology, 24(13): e20-e22 (2006).
Lange et al., CD34 modulates the trafficking behavior of hematopoietic cells in vivo, Stem Cells Dev., 16(2):297-304 (2007).
Li et al., Mimotope vaccination for epitope-specific induction of anti-CD20 antibodies, Cellular Immunology, 239:136-143 (2006).
Li et al., Murine Leukemia Induced by Retroviral Gene Marking, Science, 296: 497 (2002).
Marin et al., "Comparision of Different Suidicide Gene Strategies for the Safety Improvement of Genetically Manipulated T Cells", Blood, 116(21):1539 (2010).
Morgan et al., Case Report of a Serious Adverse Event Following the Administration of T Cells Transduced with a Chimeric Antigen Receptor Recognizing ERBB2, Molecular Therapy, 18(4):843-851 (2010).
Perosa et al., Identificationof an antigenic and immunogenic motif expressed by two 7-mer rituximab-specfic cyclic peptide mimotopes: implication for peptide-based active immunotherapy, J. Immunol., 179:7967-74 (2007).
Philip et al. A highly compact epitope-based marker suicide gene for safer and easier adoptive T-cell gene therapy, Mol. Ther., 20 (suppl 1):S35-6 (2012).
Philip et al., A highly compact epitope-based marker-suicide gene for more convenient and safer T-cell adoptive immunotherapy, Blood, 116(21):629-30 (2010).
Pule et al., A Chimeric T Cell Antigen Receptor that Augments Cytokine Release and Supports Clonal Expansion of Primary Human T Cells, Molecular Therapy, 12(5):933-941 (2005).
Pule et al., Artificial T-cell receptors, Cytotherapy, 5(3):211-226 (2003).
Pule et al., Virus-specific T cells engineered to coexpress tumor-specific receptors: persistence and antitumor activity in individuals with neuroblastoma, Nat. Med., 14(11):1264-70 (2008).
Rosenberg et al., Adoptive cell therapy for the treatment of patients with metastatic melanoma, Curr. Opin. Immunol., 21(2):233-40 (2009).
Straathof et al., An inducible caspase 9 safety switch for T-cell therapy, Blood, 105:4247-54 (2005).
Vogler et al., An improved bicistronic CD20/tCD34 vector for efficient purification and in vivo depletion of gene-modified T cells for adoptive immunotherapy, Mol. Ther., 18(7):1330-8 (2010).
Philip et al., Truncated CD34 epitope as a marker gene for clinical-grade cell sorting (poster displayed at the British Society of Gene Therapy conference in 2009).
U.S. Appl. No. 15/123,331, filed Sep. 2, 2016.

* cited by examiner

SUBSTITUTE SHEET (RULE 26)

CD20ep_v1 PYINIYNCEPANPSEKNSPSTQYCYSIQGGGS

CD20ep_v2 GCEPANPSEKNSPSTQYGGGS

Mimetope Circular GCPYSNPSLCGGGS

Mimetope Linear QDKLTQWPKWLEGGGS

FIG. 12

Approximation of distance separating CD20 binding domains of Rituximab:

Crystal structure of Rituximab bound to CD20

```
                              SEQUENCE LISTING

<160> NUMBER OF SEQ ID NOS: 24

<210> SEQ ID NO 1
<211> LENGTH: 12
<212> TYPE: PRT
<213> ORGANISM: Artificial Sequence
<220> FEATURE:
<223> OTHER INFORMATION: Rituximab-binding epitope

<400> SEQUENCE: 1

Gln Asp Lys Leu Thr Gln Trp Pro Lys Trp Leu Glu
1               5                   10


<210> SEQ ID NO 2
<211> LENGTH: 16
<212> TYPE: PRT
<213> ORGANISM: Artificial Sequence
<220> FEATURE:
<223> OTHER INFORMATION: QBEnd10-binding epitope

<400> SEQUENCE: 2

Glu Leu Pro Thr Gln Gly Thr Phe Ser Asn Val Ser Thr Asn Val Ser
1               5                   10                  15


<210> SEQ ID NO 3
<211> LENGTH: 42
<212> TYPE: PRT
<213> ORGANISM: Artificial Sequence
<220> FEATURE:
<223> OTHER INFORMATION: Stalk sequence

<400> SEQUENCE: 3

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp
        35                  40


<210> SEQ ID NO 4
<211> LENGTH: 136
<212> TYPE: PRT
<213> ORGANISM: Artificial Sequence
<220> FEATURE:
<223> OTHER INFORMATION: Polypeptide comprising RQR8 sequence

<400> SEQUENCE: 4

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
            20                  25                  30
```

-continued

```
Ala Lys Pro Thr Thr Thr Ala Cys Pro Tyr Ser Asn Pro Ser Leu Cys
        35                  40                  45

Ser Gly Gly Gly Gly Ser Pro Ala Pro Arg Pro Pro Thr Pro Ala Pro
    50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
            100                 105                 110

Ser Leu Val Ile Thr Leu Tyr Cys Asn His Arg Asn Arg Arg Arg Val
        115                 120                 125

Cys Lys Cys Pro Arg Pro Val Val
    130                 135


<210> SEQ ID NO 5
<211> LENGTH: 17
<212> TYPE: PRT
<213> ORGANISM: Artificial Sequence
<220> FEATURE:
<223> OTHER INFORMATION: Rituximab-binding epitope

<400> SEQUENCE: 5

Cys Glu Pro Ala Asn Pro Ser Glu Lys Asn Ser Pro Ser Thr Gln Tyr
1               5                   10                  15

Cys


<210> SEQ ID NO 6
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 6

Ala Cys Pro Tyr Ala Asn Pro Ser Leu Cys
1               5                   10


<210> SEQ ID NO 7
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 7

Ala Cys Pro Tyr Ser Asn Pro Ser Leu Cys
1               5                   10


<210> SEQ ID NO 8
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 8

Ala Cys Pro Phe Ala Asn Pro Ser Thr Cys
1               5                   10


<210> SEQ ID NO 9
<211> LENGTH: 10
<212> TYPE: PRT
```

<213> ORGANISM: Artificial Sequence
<220> FEATURE:
<223> OTHER INFORMATION: Rituximab-binding epitope

<400> SEQUENCE: 9

```
Ala Cys Asn Phe Ser Asn Pro Ser Leu Cys
1               5                   10
```

<210> SEQ ID NO 10
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 10

```
Ala Cys Pro Phe Ser Asn Pro Ser Met Cys
1               5                   10
```

<210> SEQ ID NO 11
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 11

```
Ala Cys Ser Trp Ala Asn Pro Ser Gln Cys
1               5                   10
```

<210> SEQ ID NO 12
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 12

```
Ala Cys Met Phe Ser Asn Pro Ser Leu Cys
1               5                   10
```

<210> SEQ ID NO 13
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 13

```
Ala Cys Pro Phe Ala Asn Pro Ser Met Cys
1               5                   10
```

<210> SEQ ID NO 14
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 14

```
Ala Cys Trp Ala Ser Asn Pro Ser Leu Cys
1               5                   10
```

<210> SEQ ID NO 15
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 15

Ala Cys Glu His Ser Asn Pro Ser Leu Cys
1 5 10

<210> SEQ ID NO 16
<211> LENGTH: 10
<212> TYPE: PRT
<213> ORGANISM: Artificial Sequence
<220> FEATURE:
<223> OTHER INFORMATION: Rituximab-binding epitope

<400> SEQUENCE: 16

Ala Cys Trp Ala Ala Asn Pro Ser Met Cys
1 5 10

<210> SEQ ID NO 17
<211> LENGTH: 82
<212> TYPE: PRT
<213> ORGANISM: Artificial Sequence
<220> FEATURE:
<223> OTHER INFORMATION: Stalk sequence with transmembrane domain and intracellular anchor

<400> SEQUENCE: 17

Pro Ala Pro Arg Pro Pro Thr Pro Ala Pro Thr Ile Ala Ser Gln Pro
1 5 10 15

Leu Ser Leu Arg Pro Glu Ala Cys Arg Pro Ala Ala Gly Gly Ala Val
20 25 30

His Thr Arg Gly Leu Asp Phe Ala Cys Asp Ile Tyr Ile Trp Ala Pro
35 40 45

Leu Ala Gly Thr Cys Gly Val Leu Leu Leu Ser Leu Val Ile Thr Leu
50 55 60

Tyr Cys Asn His Arg Asn Arg Arg Arg Val Cys Lys Cys Pro Arg Pro
65 70 75 80

Val Val

<210> SEQ ID NO 18
<211> LENGTH: 21
<212> TYPE: PRT
<213> ORGANISM: Artificial Sequence
<220> FEATURE:
<223> OTHER INFORMATION: Signal peptide

<400> SEQUENCE: 18

Met Gly Thr Ser Leu Leu Cys Trp Met Ala Leu Cys Leu Leu Gly Ala
1 5 10 15

Asp His Ala Asp Ala
20

<210> SEQ ID NO 19
<211> LENGTH: 157
<212> TYPE: PRT
<213> ORGANISM: Artificial Sequence
<220> FEATURE:
<223> OTHER INFORMATION: Polypeptide comprising RQR8 sequence and a signal peptide

<400> SEQUENCE: 19

Met Gly Thr Ser Leu Leu Cys Trp Met Ala Leu Cys Leu Leu Gly Ala
1 5 10 15

-continued

Asp His Ala Asp Ala Cys Pro Tyr Ser Asn Pro Ser Leu Cys Ser Gly
20 25 30

Gly Gly Gly Ser Glu Leu Pro Thr Gln Gly Thr Phe Ser Asn Val Ser
35 40 45

Thr Asn Val Ser Pro Ala Lys Pro Thr Thr Thr Ala Cys Pro Tyr Ser
50 55 60

Asn Pro Ser Leu Cys Ser Gly Gly Gly Gly Ser Pro Ala Pro Arg Pro
65 70 75 80

Pro Thr Pro Ala Pro Thr Ile Ala Ser Gln Pro Leu Ser Leu Arg Pro
85 90 95

Glu Ala Cys Arg Pro Ala Ala Gly Gly Ala Val His Thr Arg Gly Leu
100 105 110

Asp Phe Ala Cys Asp Ile Tyr Ile Trp Ala Pro Leu Ala Gly Thr Cys
115 120 125

Gly Val Leu Leu Leu Ser Leu Val Ile Thr Leu Tyr Cys Asn His Arg
130 135 140

Asn Arg Arg Arg Val Cys Lys Cys Pro Arg Pro Val Val
145 150 155

<210> SEQ ID NO 20
<211> LENGTH: 38
<212> TYPE: PRT
<213> ORGANISM: Artificial Sequence
<220> FEATURE:
<223> OTHER INFORMATION: QBEnd10-binding epitope and flanking residues

<400> SEQUENCE: 20

Leu Pro Ser Gly Phe Met Ser Leu Asp Asn Asn Gly Thr Ala Thr Pro
1 5 10 15

Glu Leu Pro Thr Gln Gly Thr Phe Ser Asn Val Ser Thr Asn Val Ser
20 25 30

Tyr Gln Glu Thr Thr Thr
35

<210> SEQ ID NO 21
<211> LENGTH: 33
<212> TYPE: PRT
<213> ORGANISM: Artificial Sequence
<220> FEATURE:
<223> OTHER INFORMATION: CD20ep_v1

<400> SEQUENCE: 21

Pro Tyr Ile Asn Ile Tyr Asn Cys Glu Pro Ala Asn Pro Ser Glu Lys
1 5 10 15

Asn Ser Pro Ser Thr Gln Tyr Cys Tyr Ser Ile Gln Ser Gly Gly Gly
20 25 30

Ser

<210> SEQ ID NO 22
<211> LENGTH: 22
<212> TYPE: PRT
<213> ORGANISM: Artificial Sequence
<220> FEATURE:
<223> OTHER INFORMATION: CD20ep_v2

<400> SEQUENCE: 22

Gly Cys Glu Pro Ala Asn Pro Ser Glu Lys Asn Ser Pro Ser Thr Gln
1 5 10 15

Tyr Cys Gly Gly Gly Ser
20

-continued

```
<210> SEQ ID NO 23
<211> LENGTH: 14
<212> TYPE: PRT
<213> ORGANISM: Artificial Sequence
<220> FEATURE:
<223> OTHER INFORMATION: Circular Rituximab-binding mimetope

<400> SEQUENCE: 23

Gly Cys Pro Tyr Ser Asn Pro Ser Leu Cys Gly Gly Gly Ser
1               5                   10


<210> SEQ ID NO 24
<211> LENGTH: 17
<212> TYPE: PRT
<213> ORGANISM: Artificial Sequence
<220> FEATURE:
<223> OTHER INFORMATION: Linear Rituximab-binding mimetope

<400> SEQUENCE: 24

Gln Asp Lys Leu Thr Gln Trp Pro Lys Trp Leu Glu Gly Gly Gly Gly
1               5                   10                  15

Ser
```

MARKER-SUICIDE GENE USEFUL IN ADOPTIVE CELL THERAPY

FIELD OF THE INVENTION

The present invention relates to a polypeptide useful in adoptive cell therapy (ACT). The polypeptide comprises an epitope which enables selection of transduced cells and an epitope which enables cells expressing the polypeptide to be deleted. The present invention also provides a nucleic acid encoding such a polypeptide, a cell comprising such a nucleic acid and therapeutic uses thereof.

BACKGROUND TO THE INVENTION

Adoptive cell therapy (ACT) has shown promise in clinical application against malignant and infectious disease. For example, Epstein-Barr virus-specific cytotoxic T cells (EBV-CTL) have been developed to treat posttransplantation lymphoproliferative disease (PTLD) following stem cell or organ transplantation (Brewin et al (2009) 114:4792-4803). T cells genetically engineered to recognise CD19 have been used to treat follicular lymphoma (Kochenderfer et al (2010) Blood 116:4099-4102). ACT using autologous lymphocytes genetically-modified to express anti-tumour T cell receptors has been used to treat metastatic melanoma (Rosenberg and Dudley (2009) Curr. Opin. Immunol. 21:233-240).

The reported success of tumour antigen-specific T lymphocytes for the treatment of melanoma and EBV-associated malignancies has lead to efforts to retarget effector T cells and thereby extend the range of tumours that they can treat.

T cells have been engineered which comprise T cell receptors (TCRs) with new specificities. Chimeric antigen receptors (CARs) have also been developed which comprise an antigen-binding domain, typically derived from an antibody, coupled to a signal-transducing endodomain derived from a T cell receptor. CARs thus have the specificity of an antibody coupled to the cytotoxic effector mechanisms of the T cell.

A number of clinical trials are in progress using CAR-modified T lymphocytes for immunotherapy of B-lineage malignancies (Kohn et al (2011) Mol. Ther. 19:432-438). Anti-GD2 CAR-transduced T cells are currently in clinical development for use in the treatment of neuroblastoma (Pule et al (2008) Nat. Med. 14:1264-1270). Data showing efficacy has also been reported in clinical studies of CARs in adult lymphoma. To give a further example, T-cells transduced with native T-cell receptors recognizing melanoma antigens have resulted in dramatic remissions in disseminated melanoma.

Suicide Genes

Increasing efficacy of adoptive immunotherapy has been associated with reports of serious adverse events. Acute adverse events, such as cytokine storms, have been reported after infusion of engineered T-cells. In addition, chronic adverse events have occurred and others predicted by animal models. For example, T-cells re-directed to carbonic anhydrase IX (CAIX), an antigen expressed by renal carcinoma, produced hepatotoxicity in several patients due to unexpected CAIX expression on bilary epithelium. Native T-cell receptor transfer studies against melanoma have resulted in vitiligo and iritis in patients due to expression of target antigen on skin and iris. A graft-versus host disease (GvHD) like syndrome due to TCR cross-pairing has been reported in mice after native TCR transfer. A lymphoproliferative disorder has been reported in an animal model after adoptive transfer with some CARs which incorporate co-stimulation. Finally the risk of vector insertional mutagenesis is always present. While acute toxicities can be addressed by cautious dosing, chronic toxicities are likely to be cell dose independent.

Since engineered T-cells can expand and persist for years after administration, it is desirable to include a safety mechanism to allow selective deletion of adoptively infused T-cells in the face of toxicity.

Suicide genes enable selective deletion of transduced cells in vivo. Two suicide genes are under clinical testing: HSV-TK and iCasp9.

Herpes Simplex Virus Thymidine kinase (HSV-TK) expression in T-cells confers susceptibility to ganciclovir. HSV-TK use is limited to clinical settings of profound immunosuppression such as haploidentical bone marrow transplantation as this viral protein is highly immunogenic. Further, it precludes the use of Ganciclovir for cytomegalovirus treatment.

More recently, inducible Caspase 9 (iCasp9) has been described, which can be activated by administration of a small molecule pharmaceutical (AP20187). Use of iCasp9 depends on availability of clinical grade AP20187. In addition, the use of an experimental small molecule in addition to genetically engineered cell product may cause regulatory issues.

There is thus a need for an improved suicide gene which overcome the problems associated with immunogenicity and availability of the inducing drug which are associated with known suicide genes

Marker Genes

In order to maximise efficiency of adoptive cell therapy, it is desirable to have a mechanism for monitoring transduction efficiency and selecting transduced cells. A purified population of transduced cells may then be given to the patient.

Some T-cell engineering strategies do not result in transgenic expression of readily detectable surface proteins. In these cases, measurement of transduction and tracking of cells in peripheral blood is difficult. Further, in some settings, it is essential to administer only transduced T-cells, for instance in GvHD gene-therapy protocols. Here, a marker which allows clinical grade sorting is required.

Several marker genes have been described. The first was neomycin resistance gene, now of historic interest since this xenogeneic protein only permits slow sorting by antibiotic selection. Low-affinity Nerve Growth Factor receptor has also been proposed. Although not immunogenic, it demonstrated unexpected biological effects.

More recently, truncated CD34 has been used as marker. This has the advantage that CD34 Miltenyi CliniMACS selection system is readily available for clinical grade sorting. However, it has been reported that inclusion of the transgene for CD34 may lead to aberrant homing of transduced T-cells (Lange et al (2007) Stem Cells Dev. 16:297-304).

Also, even truncated CD34 has a long coding sequence and inclusion of this protein as a marker gene is likely to tax vector packaging capacity and transcriptional efficiency.

There is thus a need for an improved marker gene which overcome the problems associated with immunogenicity, unexpected biological activity and long coding sequences which are associated with known marker genes.

DESCRIPTION OF THE FIGURES

FIG. 12. Rituximab binding epitope based on mimetope binding constructs

SUMMARY OF ASPECTS OF THE INVENTION

Figure 1:
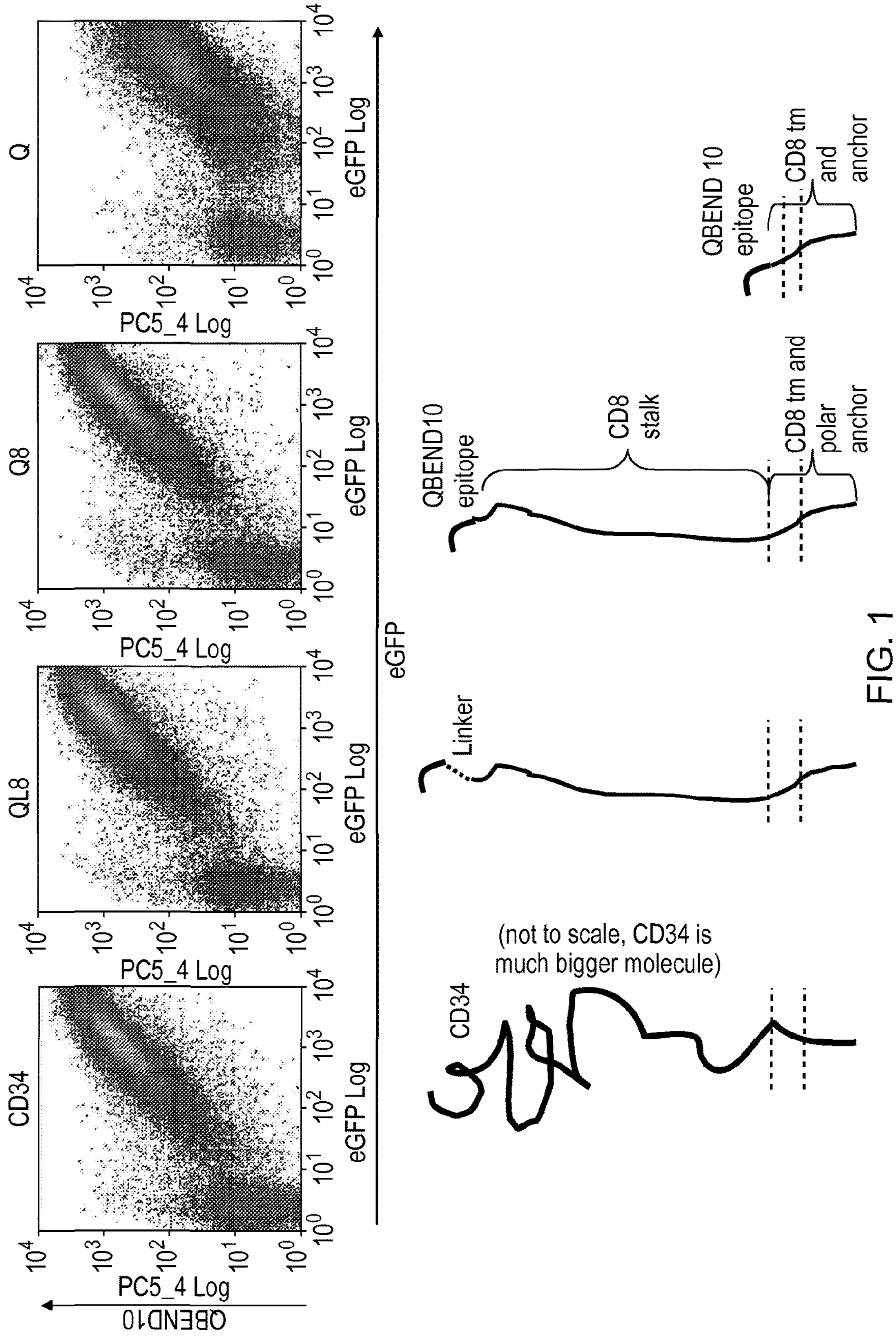
FIG. 1. QBEND10 binding to full-length CD34 (CD34), epitope fused to the CD8 stalk via a linker (QL8), without a linker (Q8), or fused directly to the CD8α transmembrane domain (Q). The retroviral vectors used co-express eGFP. It was concluded that a spacer is required for effective binding of QBEND10, but the flexible linker is not.

The present invention provides a compact polypeptide which comprises both a marker moiety and a suicide moiety. The polypeptide may be co-expressed with a therapeutic transgene, such as a gene encoding a TCR or CAR.

The marker moiety comprises a minimal epitope of CD34 which allows efficient selection of transduced cells using, for example, the Miltenyi CD34 cliniMACS system.

The suicide moiety comprises a minimal epitope based on the epitope from CD20. Cells expressing a polypeptide comprising this sequence can be selectively killed using a lytic antibody such as Rituximab.

The combined marker and suicide polypeptide is stably expressed on the cell surface after, for example, retroviral transduction of its encoding sequence.

It would be technically challenging to co-express CD20 and CD34 in addition to a therapeutic transgene (such as a transgene encoding a TCR or CAR) due to vector packaging limits and complicating biological effects of both CD34 and CD20. By providing a polypeptide comprising the binding epitopes from these proteins, the present inventors have provided a highly compact marker/suicide polypeptide, whose encoding sequence is sufficiently small to be easily packaged and co-expressed with a T-cell engineering transgene, but which retains functionality in terms of marker selection and selective deletion via the suicide moiety. By providing the binding epitopes, the combined marker/suicide polypeptide avoids biological effects associated with the full length CD20 and CD34 molecules.

Thus, in a first aspect, the present invention provides a polypeptide having the formula:

St-R1-S1-Q-S2-R2 wherein

St is a stalk sequence which, when the polypeptide is expressed at the surface of a target cell, causes the R and Q epitopes to be projected from the cell surface;

R1 and R2 are a Rituximab-binding epitopes each having the an amino acid sequence selected from the group consisting of SEQ ID No. 1, 6, 7, 8, 9, 10, 11, 12, 13, 14, 15 and 16 or a variant thereof which retains Rituximab-binding activity;

S1 and S2 are optional spacer sequences, which may be the same or different; and Q is a QBEnd10-binding epitope having the amino acid sequence shown as SEQ ID No. 2 or a variant thereof which QBEnd10-binding activity.

R1 and R2 may each have the sequence shown as SEQ ID No. 7.

The distance between R1 and R2 may be too long for the polypeptide to bind both antigen binding sites of Rituximab simultaneously.

The spacer sequences S1 and S2 may have a combined length of at least about 10 amino acids.

The distance between R1 and R2 may be more than 76.57 Å.

The stalk sequence may be derivable from CD8alpha.

The stalk sequence may comprise the amino acid sequence shown as SEQ ID No. 3.

The polypeptide may comprise the sequence shown as SEQ ID No. 4, or a variant thereof which has at least 80% identity with the sequence shown as SEQ ID No. 4 and which (i) binds QBEND10; (ii) binds Rituximab and (iii) when expressed on the surface of a cell, induces complement-mediated killing of the cell in the presence of Rituximab.

In a second aspect, the present invention provides a fusion protein which comprises a polypeptide according to the first aspect of the invention fused to a protein of interest (POI).

The POI may be a chimeric antigen receptor (CAR) or a T cell receptor (TCR).

The fusion protein may comprise a self-cleaving peptide between the polypeptide and the protein of interest.

In a third aspect, the present invention provides a nucleic acid sequence capable of encoding a polypeptide according to the first aspect of the invention or the fusion protein according to the second aspect of the invention.

In a fourth aspect, the present invention provides a vector which comprises a nucleic acid sequence according to the third aspect of the invention.

The vector may also comprise a transgene of interest which may encode a chimeric antigen receptor or a T-cell receptor.

In a fifth aspect, the present invention provides a cell which expresses a polypeptide according to the first aspect of the invention.

The cell may co-express the polypeptide and a POI at the cell surface.

There is also provided a cell which comprises a nucleic acid sequence according to the third aspect of the invention.

The cell may be a T cell.

In a sixth aspect, the present invention provides a method for making a cell according to the fifth aspect of the invention which comprises the step of transducing or transfecting a cell with a vector according to the fourth aspect of the invention.

In a seventh aspect, the present invention provides method for investigating the transduction efficiency of a gene therapy method which comprises the step of detecting expression of the QBEnd10-binding epitope on the surface of cells transfected or transduced with a vector according to the fourth aspect of the invention.

In an eighth aspect, the present invention provides method for selecting cells expressing a POI which comprises the following steps:

(i) detecting expression of the QBEnd10-binding epitope on the surface of cells transfected or transduced with a vector according to the fourth aspect of the invention; and (ii) selecting cells which are identified as expressing the OBEnd10-binding epitope.

In a ninth aspect, the present invention provides method for preparing a purified population of cells enriched for cells expressing a POI which comprises the step of selecting cells expressing a POI from a population of cells using a method according to the eighth aspect of the invention.

The method may comprise the following steps:

(i) transducing or transfecting a population of cells isolated from a patient ex vivo with a vector according to the fourth aspect of the invention; and (ii) selecting cells expressing the POI from the transduced/transfected population of cells by a method according to the eighth aspect of the invention.

In a tenth aspect, the present invention provides a cell population which is enriched for cells expressing a polypeptide according to the first aspect of the invention, and thus enriched for cells expressing a POI.

In an eleventh aspect, the present invention provides a method for tracking transduced cells in vivo which comprises the step of detection of expression of a polypeptide according to the first aspect of the invention at the cell surface.

In a twelfth aspect, the present invention provides a method for deleting a cell according to the fifth aspect of the invention, which comprises the step of exposing the cells to rituximab.

In a thirteenth aspect, the present invention provides method for treating a disease in a subject, which comprises the step of administering a cell according to the fifth aspect of the invention, or a cell population according to the tenth aspect of the invention.

The method may comprise the following steps:

(i) transduce or transfect a sample of cells isolated from a subject with a vector according to the fourth aspect of the invention, and (ii) return the transduced/transfected cells to the patient.

The method may be for treating cancer.

In a fourteenth aspect, the present invention provides a cell according to the fifth aspect of the invention or a cell population according to the tenth aspect of the invention for use in therapy by adoptive cell transfer.

DETAILED DESCRIPTION

The present invention provides a polypeptide which comprises a marker epitope and a suicide epitope.

Marker Gene

A marker gene is a protein not normally expressed by the target cell which allows for identification of successful transduction.

In the polypeptide of the present invention, a marker is used which is derived from CD34. CD34 is a cell surface glycoprotein and functions as a cell-cell adhesion factor. It also mediates the attachment of stem cells to bone marrow extracellular matrix or directly to stromal cells.

CD34 is not expressed by terminally differentiated haematopoietic lineages, so it is an ideal marker for modified T-cells.

CD34-expressing cells may be readily identified and isolated using the Miltenyi CliniMACS magnetic cell selection system, which is a commonly used reagent for clinical stem cell isolation. The CliniMACS CD34 selection system utilises the QBEnd10 monoclonal antibody to achieve cellular selection.

The present inventors have mapped the QBEnd10-binding epitope from within the CD34 antigen (see Examples) and determined it to have the amino acid sequence shown as SEQ ID No. 2.

```
                                        (SEQ ID No. 2)
                 ELPTQGTFSNVSTNVS.
```

The polypeptide of the present invention comprises a QBEnd10-binding epitope having the amino acid sequence shown as SEQ ID No. 2 or a variant thereof which retains QBEnd10-binding activity.

The term "having" as used herein is synonymous with the term "comprising".

A variant QBEnd10-binding epitope is based on the sequence shown as SEQ ID No. 2 but comprises one or more amino acid mutations, such as amino acid insertions, substitutions or deletions, provided that the epitope retains QBEnd10-binding activity. In particular, the sequence may be truncated at one or both terminal ends by, for example, one or two amino acids.

Deliberate amino acid substitutions may be made on the basis of similarity in polarity, charge, solubility, hydrophobicity, hydrophilicity, and/or the amphipathic nature of the residues as long as QBEnd10-binding activity of the epitope is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The QBEnd10-binding epitope may, for example, contain 5 or fewer, 4 or fewer, 3 or fewer, 2 or fewer or 1 amino acid mutation(s) compared to the sequence shown as SEQ ID No. 2.

The QBEnd10-binding epitope may consist essentially of the sequence shown as SEQ ID No. 2 or a variant thereof which retains QBEnd10-binding activity. The QBEnd10-binding epitope may consist of the sequence shown as SEQ ID No. 2 or a variant thereof which retains QBEnd10-binding activity.

Suicide Gene

A suicide gene encodes for a protein which possesses an inducible capacity to lead to cellular death.

In the polypeptide of the present invention, a suicide moiety is used which is based on the CD20 B-cell antigen.

CD20-expressing cells may be selectively ablated by treatment with the antibody Rituximab. As CD20 expression is absent from plasma cells, humoral immunity is retained following Rituximab treatment despite deletion of the B-cell compartment.

The Rituximab-binding epitope sequence from CD20 is CEPANPSEKNSPSTQYC (SEQ ID No. 5)

Perosa et al (2007, J. Immunol 179:7967-7974) describe a series of cysteine-constrained 7-mer cyclic peptides, which bear the antigenic motif recognised by the anti-CD20 mAb Rituximab but have different motif-surrounding amino acids. Eleven peptides were described in all, as shown in the following table:

| Peptide | Insert sequence |
|---|---|
| R15-C | acPYANPSLc (SEQ ID No. 6) |
| R3-C | acPYSNPSLc (SEQ ID No. 7) |
| R7-C | acPFANPSTc (SEQ ID No. 8) |
| R8-, R12-, R18-C | acNFSNPSLc (SEQ ID No. 9) |
| R14-C | acPFSNPSMc (SEQ ID No. 10) |
| R16-C | acSWANPSQc (SEQ ID No. 11) |
| R17-C | acMFSNPSLc (SEQ ID No. 12) |
| R19-C | acPFANPSMc (SEQ ID No. 13) |
| R2-C | acWASNPSLc (SEQ ID No. 14) |
| R10-C | acEHSNPSLc (SEQ ID No. 15) |
| R13-C | acWAANPSMc (SEQ ID No. 16) |

Li et al (2006 Cell Immunol 239:136-43) also describe mimetopes of Rituximab, including the sequence:

(SEQ ID No. 1)
QDKLTQWPKWLE.

The polypeptide of the present invention comprises a Rituximab-binding epitope having the an amino acid sequence selected from the group consisting of SEQ ID No. 1, 6, 7, 8, 9, 10, 11, 12, 13, 14, 15 and 16 or a variant thereof which retains Rituximab-binding activity.

The polypeptide of the present invention may comprise a Rituximab-binding epitope having the an amino acid sequence shown as SEQ ID No. 7 or a variant thereof which retains Rituximab-binding activity.

A variant Rituximab-binding epitope is based on the sequence selected from the group consisting of SEQ ID No. 1, 6, 7, 8, 9, 10, 11, 12, 13, 14, 15 and 16 but comprises one or more amino acid mutations, such as amino acid insertions, substitutions or deletions, provided that the epitope retains Rituximab-binding activity. In particular, the sequence may be truncated at one or both terminal ends by, for example, one or two amino acids.

Deliberate amino acid substitutions may be made on the basis of similarity in polarity, charge, solubility, hydrophobicity, hydrophilicity, and/or the amphipathic nature of the residues as long as Rituximab-binding activity of the epitope is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table presented in the previous section. Amino acids in the same block in the second column and in the same line in the third column may be substituted for each other:

The Rituximab-binding may, for example, contain 3 or fewer, 2 or fewer or 1 amino acid mutation(s) compared to the sequence selected from the group consisting of SEQ ID No. 1, 6, 7, 8, 9, 10, 11, 12, 13, 14, 15 and 16.

The Rituximab-binding may consist essentially of one of the sequences shown as SEQ ID No. 1, 6, 7, 8, 9, 10, 11, 12, 13, 14, 15 and 16 or a variant thereof which retains Rituximab-binding activity. The Rituximab-binding epitope may consist essentially of the sequence shown as SEQ ID No. 1, 6, 7, 8, 9, 10, 11, 12, 13, 14, 15 and 16 or a variant thereof which retains Rituximab-binding activity.

Where two identical (or similar) Rituximab-binding amino acid sequences are used, it may be best to use different DNA sequences to encode the two R portions. In many expression systems, homologous sequences can result in undesired recombination events. Using the degeneracy of the genetic code, alternative codons may be used to achieve DNA sequence variation without altering the protein sequence thereby preventing homologous recombination events.

Stalk Sequence

The polypeptide of the present invention comprises a stalk sequence which, when the polypeptide is expressed at the surface of a target cell, causes the R and Q epitopes to be projected away from the surface of the target cell.

The stalk sequence causes the R and Q epitopes to be sufficiently distanced from the cell surface to facilitate binding of, for example, Rituximab and/or QBEnd10.

The stalk sequence elevates the epitopes from the cell surface.

The stalk sequence may be a substantially linear amino acid sequence. The stalk sequence may be sufficiently long to distance the R and Q epitopes form the surface of the target cell but not so long that its encoding sequence compromises vector packaging and transduction efficiency. The stalk sequence may, for example be between 30 and 100 amino acids in length. The stalk sequence may be approximately 40-50 amino acids in length.

The stalk sequence may be highly glycosylated.

The stalk sequence may comprise or be approximately equivalent in length to the sequence:

(SEQ ID No. 3)
PAPRPPTPAPTIASQPLSLRPEACRPAAGGAVHTRGLDFACD

The stalk sequence may additionally comprise a transmembrane domain, optionally together with an intracellular anchor sequence. The transmembrane domain and intracellular anchor sequence may be derived from the same protein as extracellular part of the stalk sequence or it/they may be derived from a different protein. The transmembrane domain and intracellular anchor sequence may be derivable from CD8.

A CD8 stalk sequence which comprises a transmembrane domain and an intracellular anchor may have the following sequence:

(SEQ ID No. 17)
<u>PAPRPPTPAPTIASQPLSLRPEACRPAAGGAVHTRGLDFACD</u>IYIWAPLA

GTCGVLLLSLVITLYCNHRNRRRVCKCPRPVV.

Within this sequence, the underlined portion corresponds to the CD8α stalk; the central portion corresponds to the transmembrane domain; and the portion in bold corresponds to the intracellular anchor.

Spacers

The polypeptide of the present invention has the formula:

St-R1-S1-Q-S2-R2 in which

St is a stalk sequence

R1 and R2 are rituximab-binding epitopes; and

Q is a QBEnd10-binding epitope.

In the above formula, S1 and S2 are optional spacer sequences, which may be the same or different.

Rituximab is a classical antibody molecule having two antigen binding sites, one at each tip of the Y-shaped molecule.

The spacer sequences may be of a length and configuration such that, when the polypeptide is expressed at the cell surface, the distance between R1 and R2 is too long for the polypeptide to bind both antigen binding sites of a Rituximab molecule simultaneously.

The spacer sequences S1 and S2 may have a combined length of at least about 10 amino acids.

In the expressed polypeptide, the distance between R1 and R2 may be more than 76.57 Å. For example, the length and configuration of the spacer sequences may be such that the distance between R1 and R2 is at least 78, 80 or 85 Å. For the purposes of this calculation, the molecular distance between separate amino acids in a linear back bone can be assumed to be approximately 3 Å per amino acid.

The linker sequence(s) may be substantially linear. They may comprise or consist of serine and glycine residues. The linker sequence(s) may have the general formula:

S-(G)n-S where S is serine, G is Glycine and n is a number between 2 and 8. The, or each, linker may comprise or consist of the sequence S-G-G-G-S.

The combined length of the Q epitope and spacer(s) (i.e. the length of the S1-Q-S2 portion of the peptide may be at least 28 amino acids.

RQR8 Sequence

The polypeptide of the invention may comprise or consist of the 136 amino acid sequence shown as SEQ ID. No. 4.

(SEQ ID No. 4)
CPYSNPSLCSGGGGSELPTQGTFSNVSTNVSPAKPTTTACPYSNPSLCSG

GGGSPAPRPPTPAPTIASQPLSLRPEACRPAAGGAVHTRGLDFACDIYIW

APLAGTCGVLLLSLVITLYCNHRNRRRVCKCPRPVV

The polypeptide may also comprise a signal peptide at the amino terminus. The signal peptide may, for example, comprise or consist of the sequence shown as SEQ ID No. 18

(SEQ ID No. 18)
MGTSLLCWMALCLLGADHADA

A polypeptide comprising such a signal peptide and the 136 amino acid sequence given above would thus have the following 157 amino acid sequence:

(SEQ ID No. 19)
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDIYIWAPLAGTCGVLLLSLVITLYCNHRNRRRVC

KCPRPVV

Once the polypeptide is expressed by the target cell, the signal peptide is cleaved, resulting in the 136aa mature peptide product.

Native CD34 protein is 385 amino acid residues in length therefore over 1 kb of DNA sequence is required for full length CD34 expression. Thus the entire RQR8 construct is approximately ⅓ the size of the CD34 protein alone.

The RQR8 construct is thus a much more manageable size than the full length CD34 marker gene. It has the added advantage of comprising a suicide gene element with lytic sensitivity at least equal to that demonstrated by full-length CD20.

The polypeptide of the invention may comprise or consist of a variant of the sequence shown as SEQ ID No. 4, which has at least 70%, 80% or 90% identity with the sequence shown as SEQ ID No. 4, as long as it retains the functional activity of the SEQ ID No. 4 polypeptide. For example the variant sequence should (i) bind QBEND10; (ii) bind Rituximab and (iii) when expressed on the surface of a cell, induce complement-mediated killing of the cell in the presence of Rituximab.

Homology comparisons may be conducted by eye or with the aid of readily available sequence comparison programs, such as the GCG Wisconsin Bestfit package.

Fusion Protein

The polypeptide of the invention may be in the form of a fusion protein, in which the polypeptide is fused to a protein of interest (POI).

The fusion protein may comprise a self-cleaving peptide between the polypeptide and the protein of interest. Such a self-cleaving peptide should allow co-expression of the polypeptide and the POI within the target cell, followed by cleavage so that the polypeptide and POI are expressed as separate proteins at the cell surface. For example, the fusion protein may comprise the foot-and-mouth disease self-cleaving 2A peptide.

Protein of Interest

The protein of interest is a molecule for expression at the surface of a target cell. The POI may exert a therapeutic or prophylatic effect when the target cell is in vivo.

The POI may be a chimeric antigen receptor (CAR) or a T cell receptor (TCR).

Chimeric antigen receptors are generated by joining an antigen-recognising domain (ectodomain) to the transmembrane and intracellular portion of a signalling molecule (endodomain). The ectodomain is most commonly derived from antibody variable chains (for example an ScFv), but may also be generated from T-cell receptor variable domains or other molecules. The endodomain may comprise the intracellular portion of CD3-ζ. The endodomain may comprise a CD28-OX40-CD3ζ; tripartite cytoplasmic domain.

The POI may be a CAR or TCR with specificity for a tumour-associated antigen, i.e. a protein which is expressed or overexpressed on cancer cells. Such proteins include ERBB2 (HER-2/neu), which is overexpressed in 15-20% of breast cancer patients and is associated with more aggressive disease; CD19, which is expressed on most B-cell malignancies; carboxy-anhydrase-IX, which is frequently overexpressed in renal cell carcinoma; GD2, which is expressed by neuroblastoma cells; p53; MART-1 (DMF5); gp100:154; NY-ESO-1; and CEA.

Nucleic Acid Sequence

The second aspect of the invention relates to a nucleic acid sequence capable of encoding a polypeptide or fusion protein of the invention.

The nucleic acid, when expressed by a target cell, causes the encoded polypeptide to be expressed at the cell-surface of the target cell. Where the nucleic acid encodes both the polypeptide and POI (for example as a fusion protein), it should cause both the polypeptide of the invention and the POI to be expressed at the surface of the target cell.

The nucleic acid sequence may be RNA or DNA, such as cDNA.

Vector

The present invention also provides a vector which comprises a nucleic acid sequence of the present invention. The vector may also comprise a transgene of interest, i.e. a gene encoding a POI.

The vector should be capable of transfecting or transducing a target cell, such that they express the polypeptide of the invention and optionally a protein of interest.

The vector may be a non-viral vector such as a plasmid.

The vector may be a viral vector, such as a retroviral or lentiviral vector.

The vector may comprise a nucleic acid encoding the polypeptide and a nucleic acid comprising the POI as separate entities, or as a single nucleotide sequence. If they are present as a single nucleotide sequence they may comprise one or more internal ribosome entry site (IRES) sequences between the two encoding portions to enable the downstream sequence to be translated.

Cell

The present invention also provides a cell which expresses a polypeptide according to the first aspect of the invention. The cell may coexpress the polypeptide and a POI at the cell surface.

The present invention also provides a cell which comprises a nucleic acid sequence capable of encoding a polypeptide according to the first aspect of the invention.

The cell may have been transduced or transfected with a vector according to the invention.

The cell may be suitable for adoptive cell therapy.

The cell may be a T cell, such as a cytotoxic T lymphocyte (CTL). The T cell may have an existing specificity. For example, it may be an Epstein-Barr virus (EBV)-specific T cell.

The cell may be derived from a patient. For example, the cell may have been removed from a patient and then transduced ex vivo with a vector according to the present invention.

T cell populations which are suitable for ACT include: bulk peripheral blood mononuclear cells (PBMCs), CD8+ cells (for example, CD4-depleted PBMCs); PBMCs that are selectively depleted of T-regulatory cells (Tregs); isolated central memory (Tcm) cells; EBV-specific CTLs; and tri-virus-specific CTLs.

The present invention also comprises a cell population which comprises a cell according to the present invention. The cell population may have been transduced with a vector according to the present invention. A proportion of the cells of the cell population may express a polypeptide according to the first aspect of the invention at the cell surface. A proportion of the cells of the cell population may co-express a polypeptide according to the first aspect of the invention and a POI at the cell surface. The cell population may be ex vivo patient-derived cell population.

Selection Using the Marker Sequence

The present invention provides a method for measuring transduction with a trangene of interest (which encodes a protein of interest POI), which comprises the step of transducing a population of cells with a vector which coexpresses the polypeptide of the invention and the protein of interest and detecting expression of the QBEnd10-binding epitope on the surface of cells, wherein the proportion of cells expressing the polypeptide of the invention corresponds to the proportion of cells transduced with the transgene of interest.

The present invention also provides a method for selecting cells expressing a POI which comprises the following steps:

(i) detecting expression of the QBEnd10-binding epitope on the surface of cells transfected or transduced with a vector of the present invention which comprises a nucleotide sequence encoding the POI; and (ii) selecting cells which are identified as expressing the QBEnd10-binding epitope.

Cells may be sorted using the Miltenyi CD34 cliniMACS system. This system is well adapted for use in clinical grade sorting in a GMP facility.

Cells expressing the QBEnd10-binding epitope may be identified and/or sorted by methods known in the art such as FACS.

The present invention also provides a method for preparing a purified population of cells enriched for cells expressing a POI which comprises the step of selecting cells expressing a POI from a population of cells using the method described above.

The present invention also provides a purified population of POI-expressing cells prepared by such a method.

In the purified population of cells, at least 80%, 85%, 90% or 95% of the cells may express a POI (and a polypeptide according to the present invention).

The present invention also provides a method for tracking transduced cells in vivo which comprises the step of detection of expression of the polypeptide of the invention at the cell surface. Cells may be tracked in vivo by methods known in the art such as bioluminescence imaging. For such applications, the polpeptide of the invention may be engineered to be co-expressed with a detectable protein, such as luciferase.

Deletion Using the Suicide Sequence

The present invention also provides a method for deleting cells transduced by a vector according to the present invention, which comprises the step of exposing the cells to complement and rituximab.

When the polypeptide of the invention is expressed at the surface of a cell, binding of rituximab to the R epitopes of the polypeptide causes lysis of the cell.

More than one molecule of Rituximab may bind per polypeptide expressed at the cell surface. Each R epitope of the polypeptide may bind a separate molecule of Rituximab.

Deletion of cells may occur in vivo, for example by administering Rituximab to a patient.

The decision to delete the transferred cells may arise from undesirable effects being detected in the patient which are attributable to the transferred cells. For example, unacceptable levels of toxicity may be detected.

Therapeutic Method

Adoptive transfer of genetically modified T cells is an attractive approach for generating desirable immune responses, such as an anti-tumour immune response.

The present invention provides a method for treating and/or preventing a disease in a subject, which comprises the step of administering a cell according to the invention to the subject. The method may comprise the step of administering a population of cells to a subject. The population of cells may be enriched for cells expressing a transgene of interest using a method described above.

The method may involve the following steps:

(i) taking a sample of cells, such as a blood sample from a patient, (ii) extracting the T-cells, (iii) transducing or transfecting the T cells with a vector of the present invention which comprises a nucleic acid sequence encoding the marker/suicide sequence and a transgene of interest, (iv) expanding the transduced cells ex-vivo (v) returning the cells to the patient.

The transduced cells may possess a desired therapeutic property such as enhanced tumour specific targeting and killing.

The cells of the present invention may be used to treat a cancer. As explained in Rosenburg and Dudley (2009—as above), virtually all tumours are equally susceptible to lysis using an ACT approach and all are able to stimulate cytokine release from anti-tumour lymphocytes when tumour antigen is encountered.

The cells of the present invention may, for example, may be used to treat lymphoma, B-lineage malignancies, metastatic renal cell carcinoma (RCC), metastatic melanoma or neuroblastoma.

Alternatively the cells of the invention may be used to treat or prevent a non-cancerous disease. The disease may be an infectious disease or a condition associated with transplantation.

The cells of the invention may be used to treat or prevent post-transplantation lymphoproliferative disease (PTLD)

The invention will now be further described by way of Examples, which are meant to serve to assist one of ordinary skill in the art in carrying out the invention and are not intended in any way to limit the scope of the invention.

EXAMPLES

Example 1

Epitope Mapping the QBEnd10 Epitope from the CD34 Antigen

The present inventors first sought to find the epitope of CD34 which binds QBEND10, the antibody used in Miltenyi CliniMACS CD34 selection system. To this end, they generated a retroviral library of putative QBEnd10 binding epitopes from the native CD34 antigen.

Figure 11:
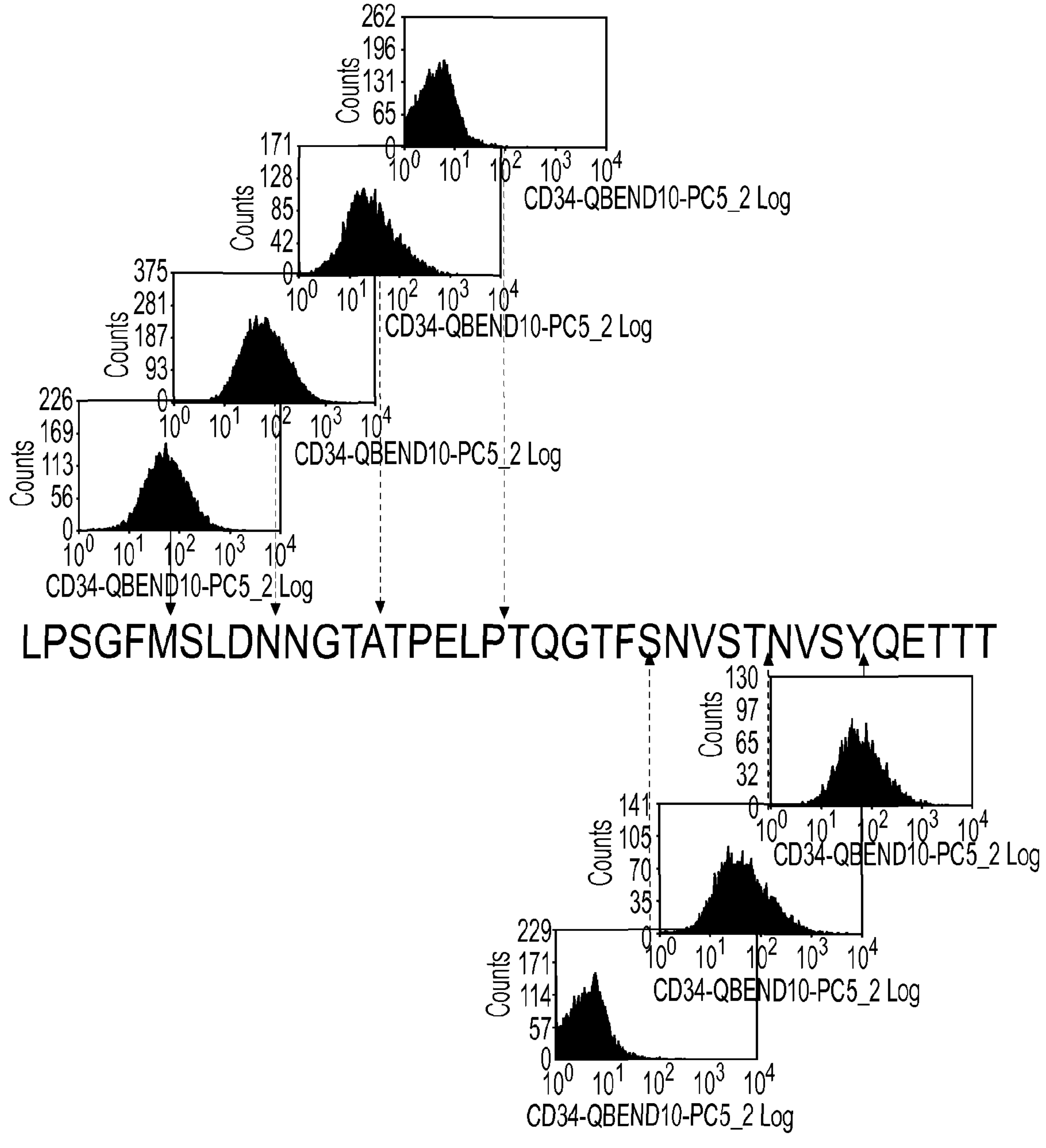
FIG. 11. Finer epitope mapping of QBEnd10 binding

Having isolated a QBEnd10 binding domain, further minimisation of the QBEnd10 binding epitope was achieved using a bi-directional deletion strategy (FIG. 11).

A final minimal epitope binding construct was derived containing only 16 amino acid residues and having the sequence ELPTQGTFSNVSTNVS.

Example 2

Introducing a Spacer to Distance the CD34 Epitope from the Cell Surface

Various stalk and linker combinations were tested in order to investigate improvements in presentation of the epitope. To test the binding efficacy of the marker-gene, a bicistronic vector was used expressing eGFP as a marker of successful transfection.

The stalk used was derived from CD8alpha. This highly glycosylated structure acts as an effective spacer, elevating the epitope from the cell surface. It is relatively short in length: only 49 amino acids long.

Figure 2:
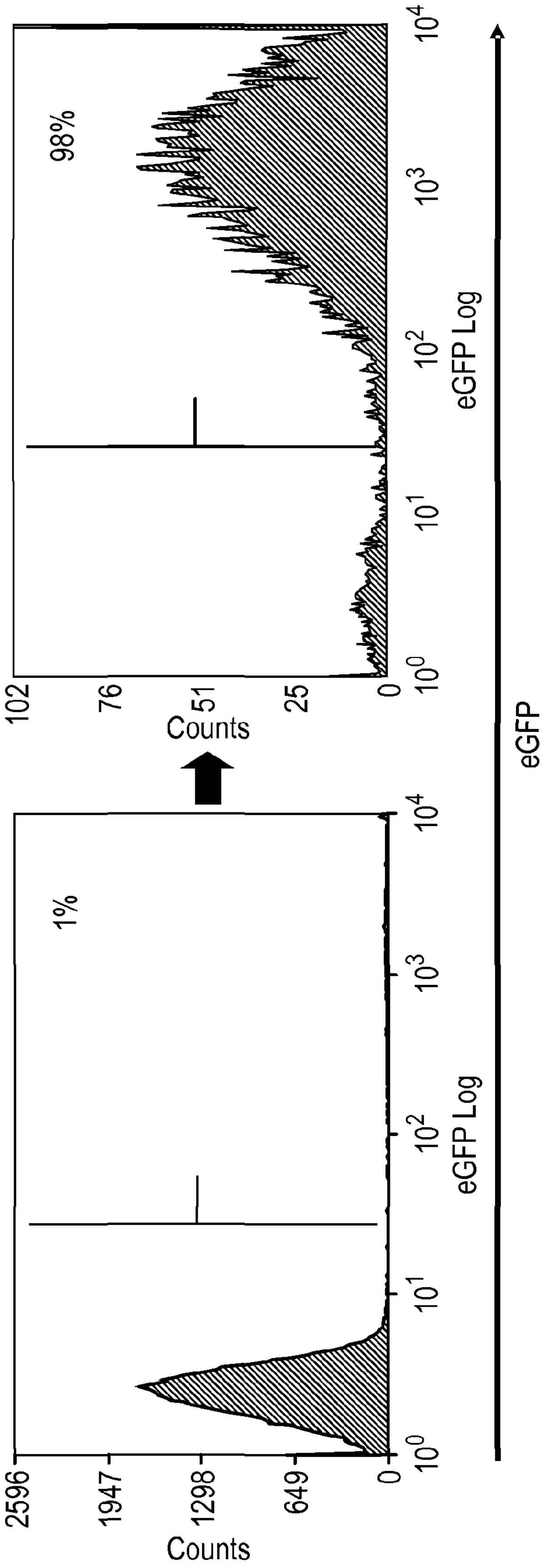
FIG. 2. T-cells transduced with a low titre supernatant could be enriched to near purity using Miltenyi CD34 selection kit.

Three constructs were considered: two CD8 stalk-bound constructs, with and without a flexible linker sequence, to project the putative epitope away from the cell surface, compared against a smaller membrane-proximal construct. The CD8 stalk-bound construct could achieve equal binding of QBEND10 as for full-length CD34 (FIG. 1). T-cells transduced with this construct were shown to be readily magnetically sorted using Miltenyi QBEnd10 beads (FIG. 2).

Example 3

Inclusion of a Rituximab-Binding Epitope

The present inventors decided to epitope map the CD20 B-cell antigen as a putative suicide gene. Rituximab is highly lytic for CD20 expressing targets. Recent crystallographic data has identified the Rituximab-binding interaction as being localised to the large extracellular loop. Based on this data, the present inventors generated a pair of constructs expressing versions of this minimal loop structure.

They first co-expressed different fragments of the CD20 major extracellular loop identified by crystallography to be the Rituximab binding site. These constructs failed to bind Rituximab.

Figure 3:
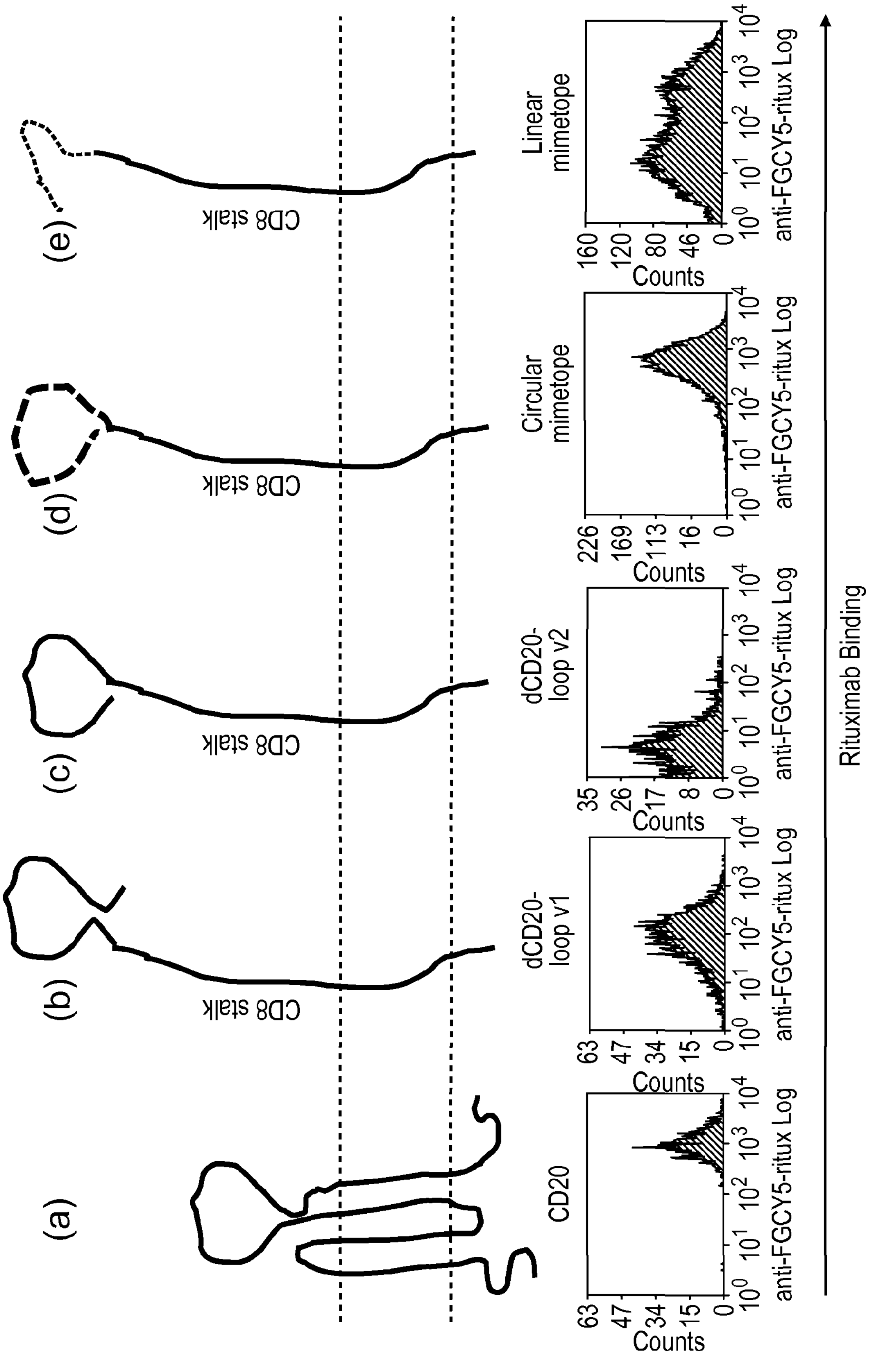
FIG. 3. Different attempts at Rituximab binders with binding by FACS shown beneath: (*a*) Full length CD20. Remainder all attached to CD8 stalk. (*b*) Major extracellular loop of CD20 including 5 residues on either side of the disulfide bond; (*c*) Major extracellular loop of CD20 from the disulfide bond cysteines; (*d*) The circular mimetope from Perosa (2007, J. Immunol 179:7967-7974); (*e*) the linear mimetope from Perosa (2007, as above). Construct (*d*) was selected since other constructs failed to bind, bound poorly or gave a bi-phasic binding pattern.

Next, they tried linear and circular Rituximab-binding mimetopes (described by Perosa et al (2006) as above). Mimetopes are peptide sequences identified by phage display, which demonstrate good binding of a target antibody. They selected both a circular mimetope, constrained by disulphide bonds, and a linear mimetope for consideration (FIG. 12). Inclusion of the circular mimetope (11 amino acids) afforded excellent Rituximab binding (FIG. 3).

Figure 13:
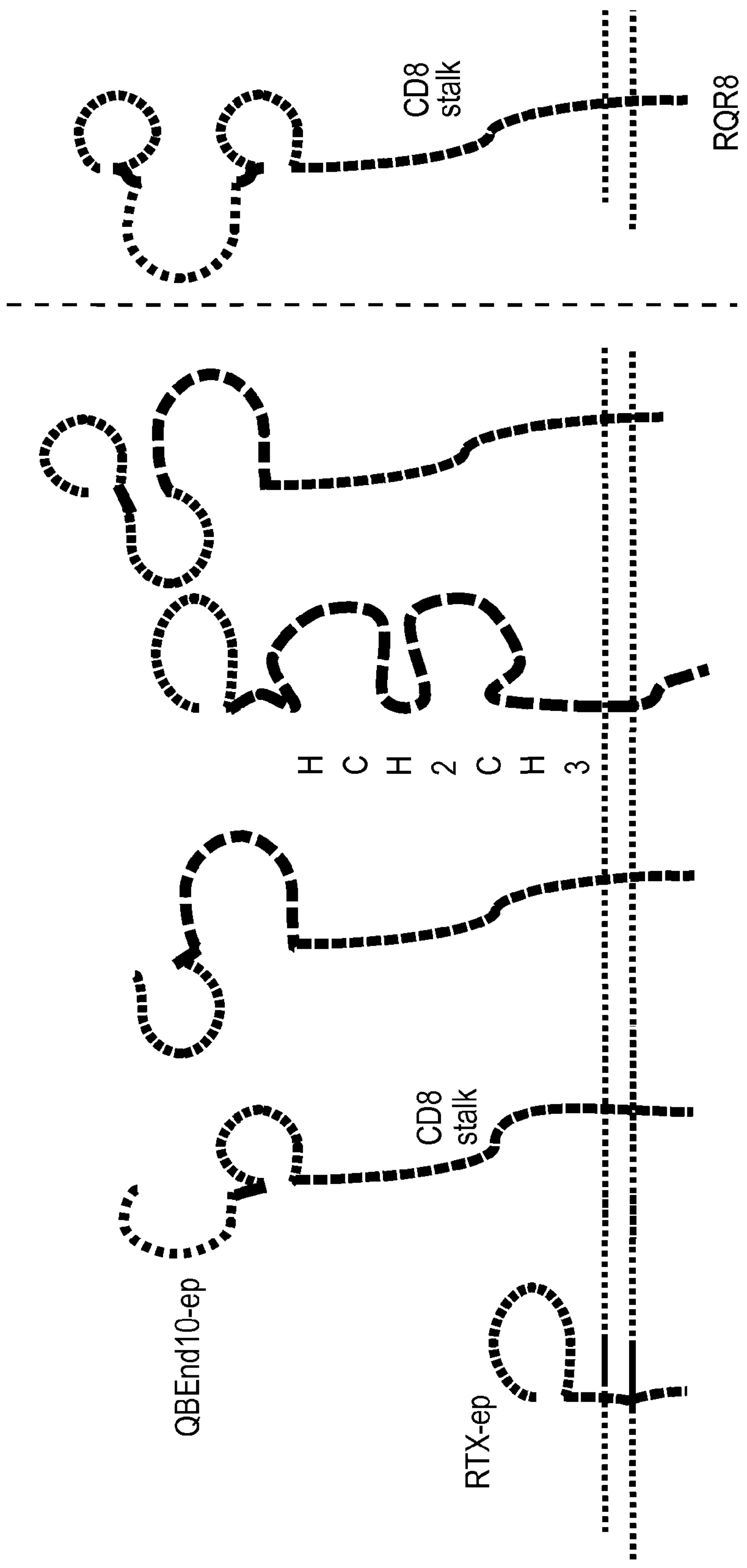
FIG. 13. Re-engineered constructs

Having demonstrated effective Rituximab binding, they then performed functional assays to assess the functional efficacy of the combination constructs using in vitro CDC assays. However, complement mediated killing was poor at only 65% (data not shown). Variant constructs were generated in an attempt to solve this problem (FIG. 13).

Figure 4:
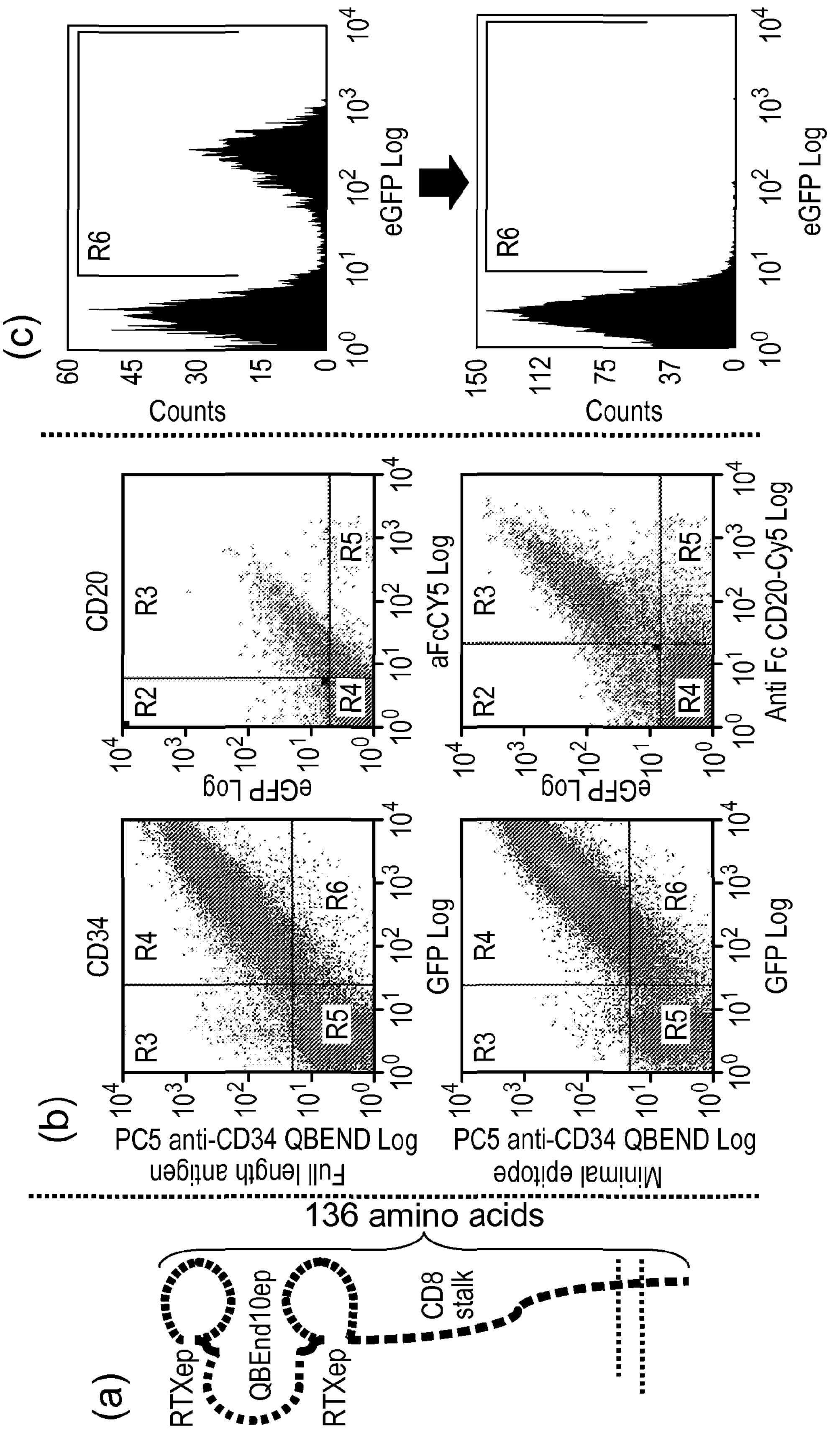
FIG. 4. (*a*) Cartoon showing structure of RQR8; (*b*) QBEND10 binding is compared with that of full-length CD34 (left); Rituximab binding to RQR8 is compared with that to full-length CD20 (right). Note, eGFP is co-expressed (*c*) Killing efficiency after exposure to complement and rituximab gating on live cells shows deletion of practically all transduced T-cells.
Figure 14:
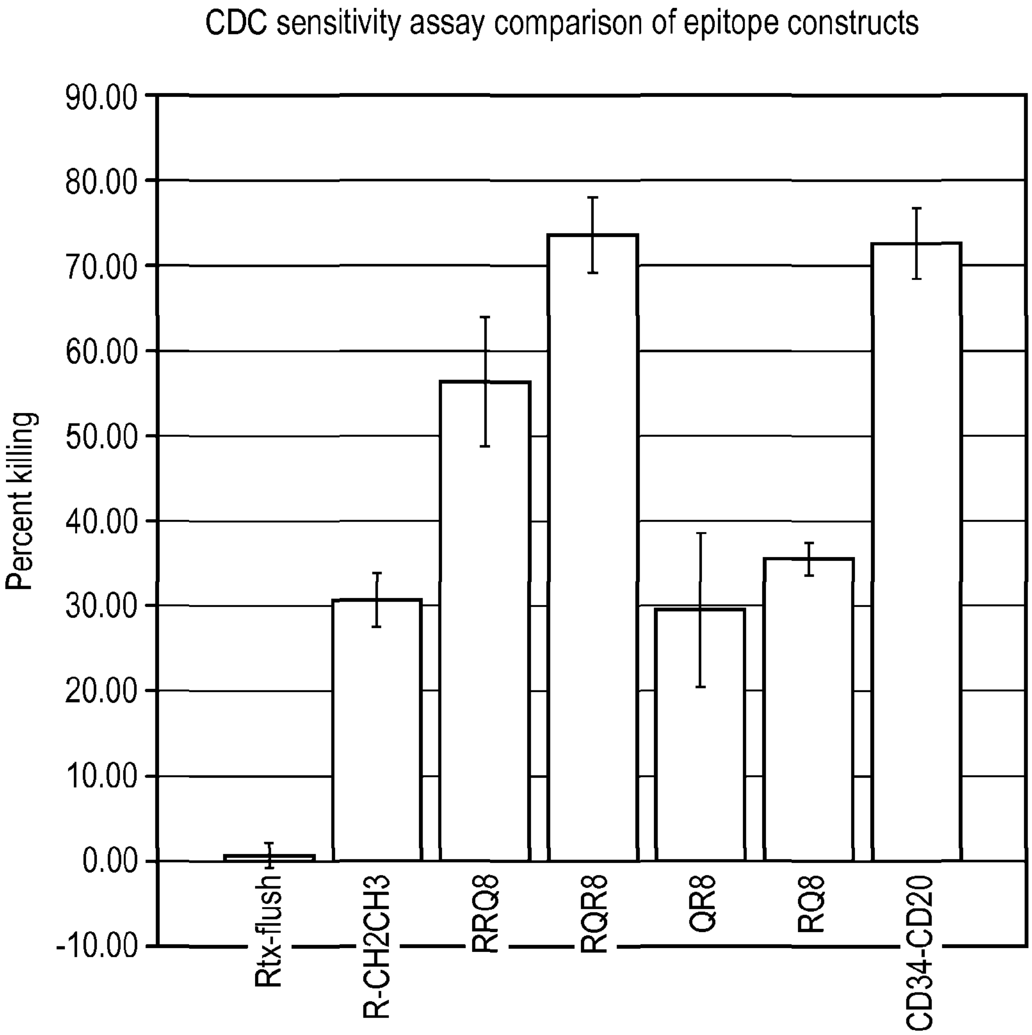
FIG. 14. CDC assay with re-engineered constructs.

A final construct comprising of two CD20 circular mimetopes flanking a single QBEnd10 epitope on the CD8 stalk allowed optimal QBend10 and Rituximab binding, as well as highly effective complement mediated killing (designated RQR8, FIGS. 4 and 14).

This RQR8 construct is only 136 amino acids long. The binding of QBEND10 is similar to that of full-length CD34. T-cells transduced with RQR8 could be effectively sorted using CD34 cliniMACS (data not shown). Binding of Rituximab was 3.4 fold increased relative to native CD20. Complement mediated killing could delete >97% of transduced sorted T-cells.

Example 4

Construction of Murine IgG2a Version of Rituximab

Rituximab, with its human IgG1 constant regions, is not particularly lytic in mice. The hybridoma IDEC-2B8 is a source of Rituximab variable regions but is a mouse IgG1 hybridoma. To produce a murine equivalent to Rituximab, it was necessary to generate a mouse IgG2a version. The present inventors cloned the heavy and light chain variable regions in frame with mouse kappa/IgG2a constant regions. A recombinant mAb (termed Ritux-mG2a) was then generated from suspension K562 cells. This binds RQR8 (FIG. 8), and is the functional equivalent to Rituximab in the mouse model in terms of complement mediated lysis and ADCC.

Example 5

The Use of RQR8 for T-Cell Cancer Gene Therapy Applications

Figure 5:
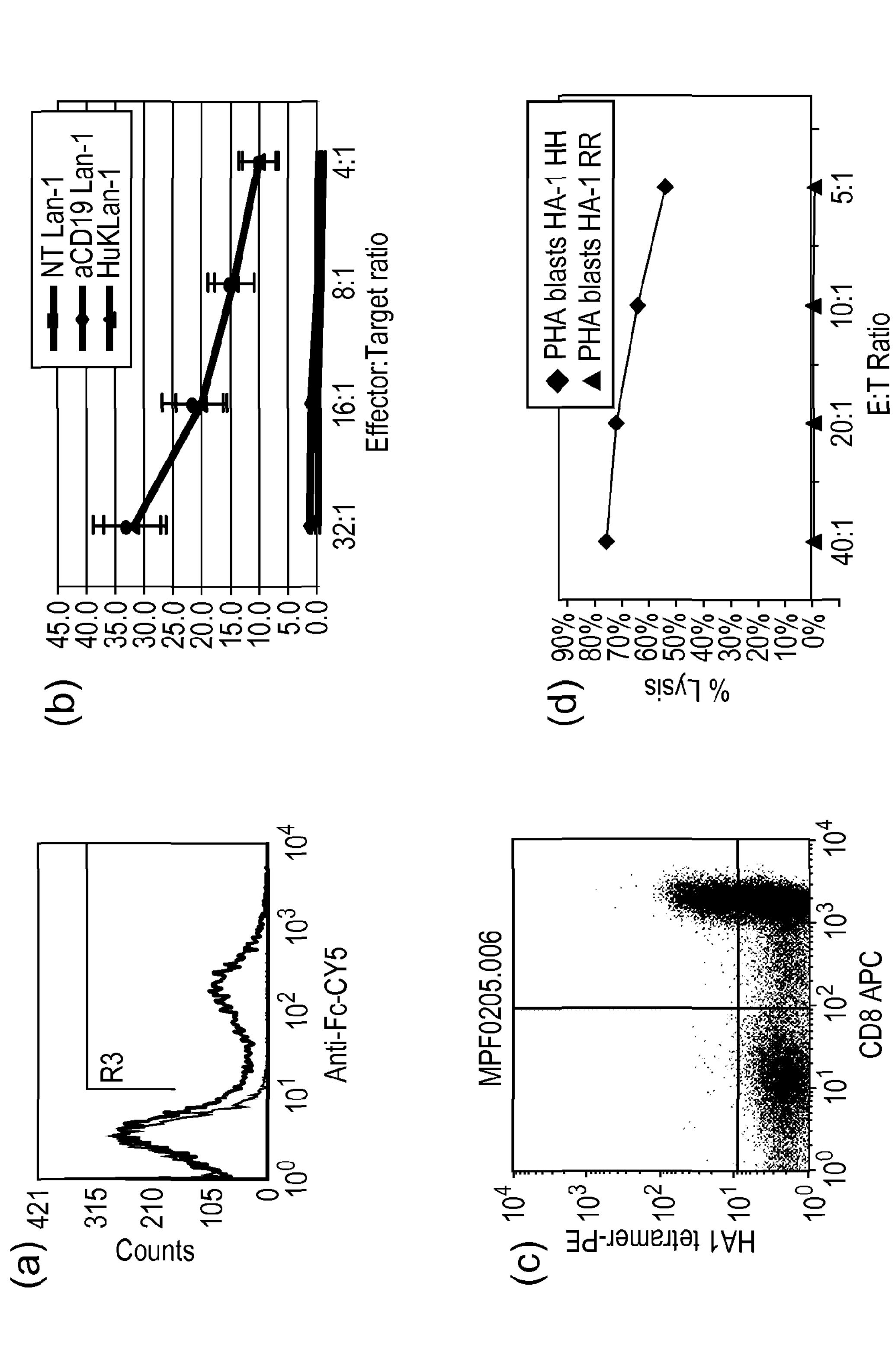
FIG. 5. (*a*) Expression of a $3^{rd}$ generation anti-GD2 CAR on human T-cells detected by FACS and (*b*) function of non-transduced T-cells (NT), anti-CD19 T-cells and anti-GD2 T-cells (HuK) in chromium release assay against GD2+ target cell line. (*c*) A native TCRαβ which recognizes HA-1 minor histocompatibility antigen expressed on EBV-specific CTLs detected by tetramer staining. (*d*) Killing of HA-1 positive HLA-A2+ PHA blasts (HH), and absence of killing of HA-1 negative (RR) HLA-A2+ blasts by these transduced EBV-CTLs.

The present inventors have previously generated a $3^{rd}$ generation anti-GD2 chimeric antigen receptor [FIG. 5 (*a*) and (*b*)]. They have also optimized a HA-$1^{18}$ native TCR native TCR for transgenic expression [FIGS. 5(*c*) and (*d*)]. Both have been co-expressed with RQR8.

Figure 8:
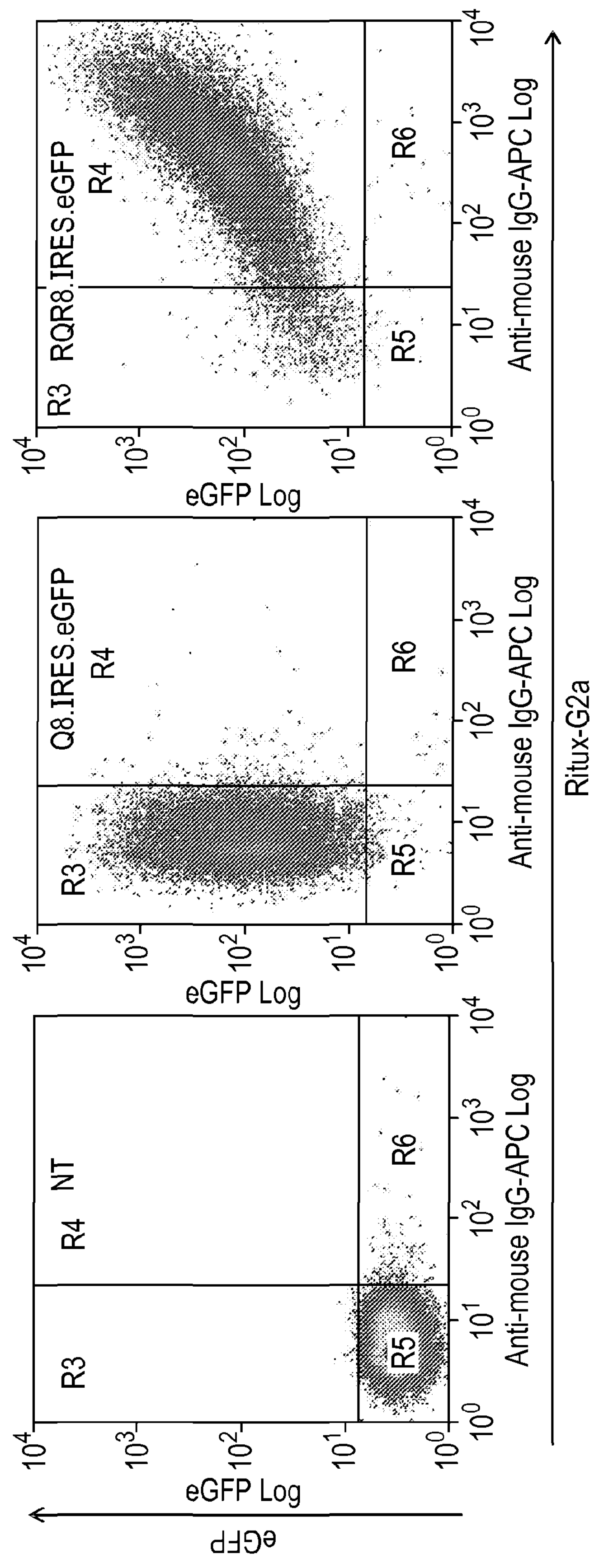
FIG. 8. Binding of the recombinant Ritux-murine IgG2a antibody (Ritux-mG2a) to non-transduced Jurkat T-cells, Jurkat T-cells transduced with QBEnd10 epitope only construct and Jurkat T-cells transduced with RQR8 construct only. (eGFP is co-expressed.)
Figure 9:
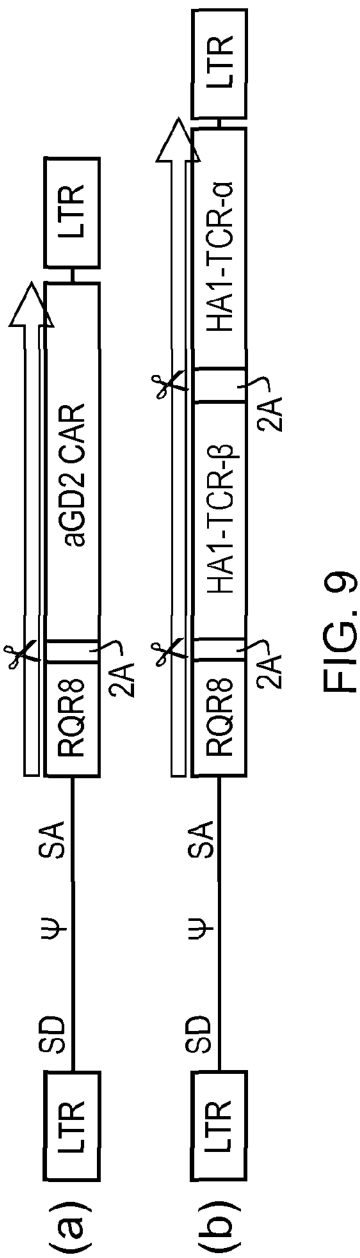
FIG. 9. Constructs co-expressing RQR8 with either (*a*) anti-GD2 CAR or anti-HA1 native TCR FIG. 10. Proposed constructs with (*a*) Qbend10 epitope on the CD8 stalk (Q8, as a control), (*b*) RQR8 on its own, or Q8 co-expressed with either (*c*) iCasp9 or (*d*) HSV-TK. Constructs engineered to co-express Firefly Luciferase (FLuc) are also shown.

Two test constructs are constructed in which the RQR8 gene is co-expressed with either (a) a CAR or (b) a native TCR (FIG. 8). The foot-and-mouth disease self-cleaving 2A peptide allows co-expression.

Efficiency of co-expression/2A cleavage is tested in normal donor T-cells by flow cytometry (as shown in FIG. 5) and Western blotting. The function of unsorted and sorted transduced T-cells is compared by Chromium release assay, proliferation, and cytokine bead array in response to targets and controls.

The extended phenotype of sorted and unsorted T-cells is also characterised. Loss of effector activity of transduced bulk populations is measured before and after depletion with Rituximab/complement.

Example 6

In Vivo Testing of RQR8 and In Vivo Comparison with Other Suicide Genes

Figure 6:
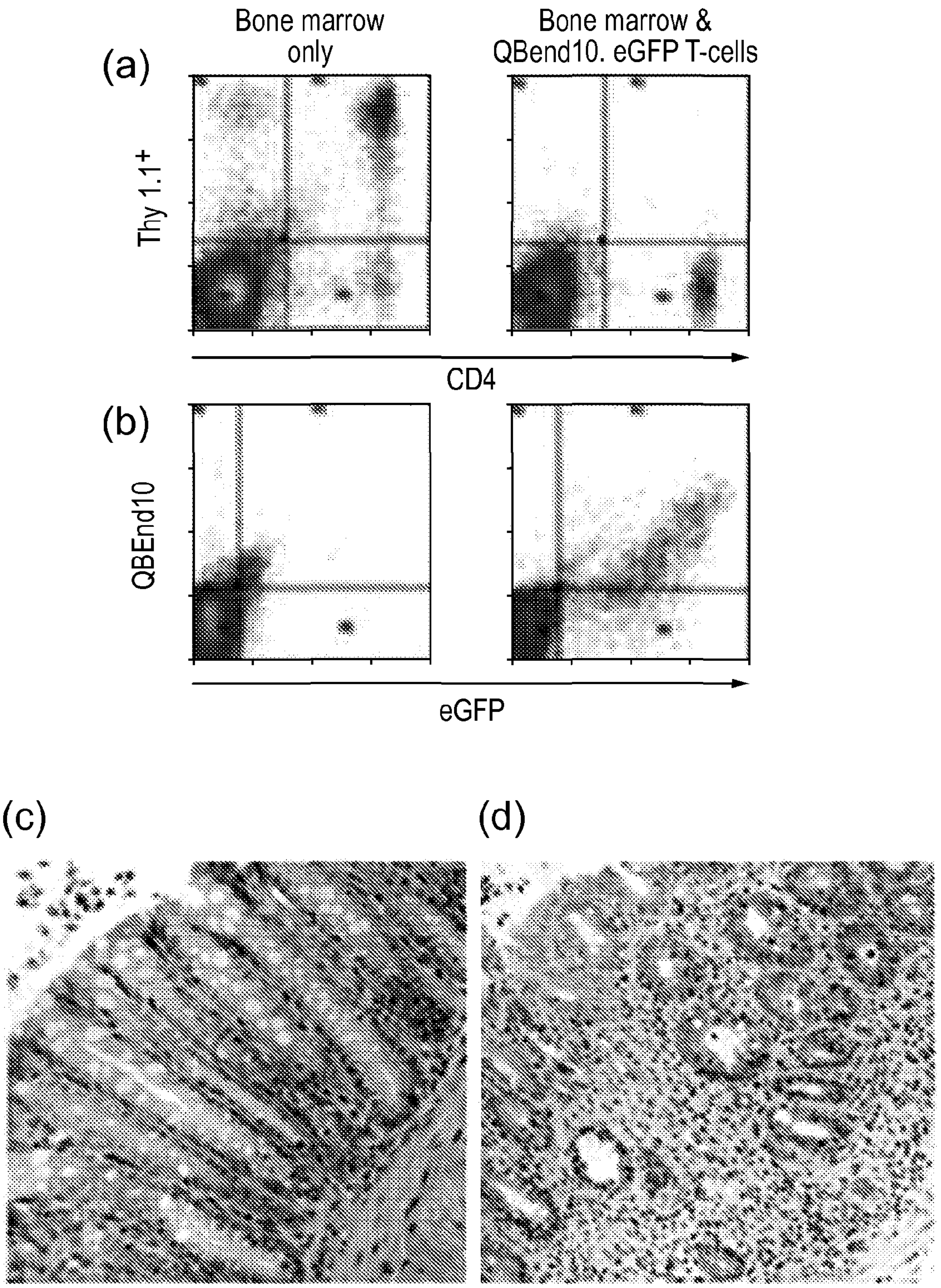
FIG. 6. Model of GvHD. Balb/c recipient mice were irradiated and received $10^7$ T-depleted bone marrow cells from C57BL/6 mice. Control mouse received no additional cells; test mouse received $3\times10^6$ magnetically sorted C57BL/6 splenocytes transduced with RQR8. (*a*) FACS of splenocytes stained for CD4 and Thy1.1 on day 29 after BMT. Residual recipient lymphocytes (Thy1.1$^+$) are present in the control mouse but not in the recipient mouse indicating GvHD. (*b*) Splenocytes again at day 29 stained with QBEnd10-transduced lymphocytes can be seen engrafted in the recipient mouse. (*c*) Bowel histology of control mouse and (*d*) recipient mouse showing clear gut GvHD in the latter.
Figure 10:
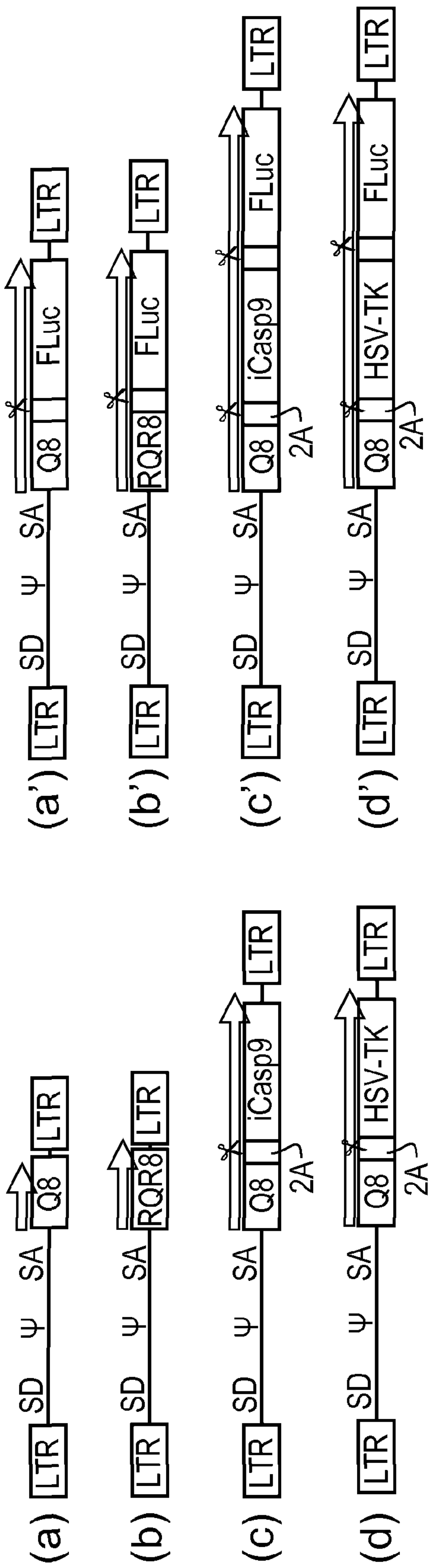

The present inventors have developed a mouse model of GvHD. Splenocytes transduced with RQR8 cause GvHD after administration (FIG. 6). In order to test RQR8 in vivo, transplanted mice receive either splenocytes transduced with RQR8-2A-FLuc or control Q8-2A-FLuc [(a') and (b') FIG. 10]. Ritux-mG2a is administered at day 10 when GvHD is evident by weight loss to half of the mice.

Figure 7:
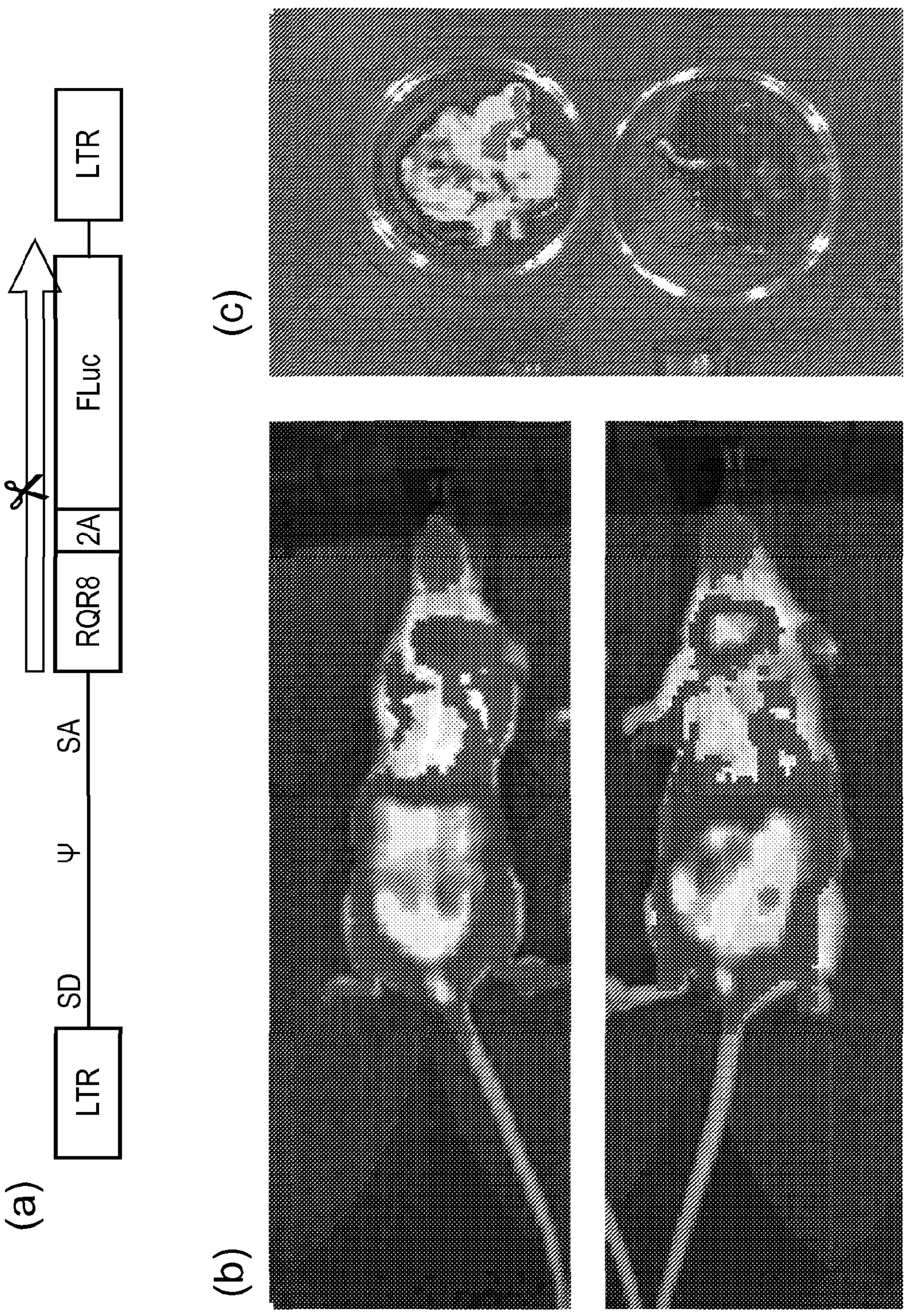
FIG. 7. BLI of transduced splenocytes in mouse model of GvHD. (*a*) We have cloned RQR8 in frame with our red-shifted, codon-optimized firefly Luciferase separated by self-cleaving 2A sequence (RQR8-2A-FLuc). (*b*) Black 6 splenocytes were transduced with above vector, sorted and administered as DLI. Bioluminescent imaging was performed 7 days later on (*b*) live animals, and (*c*) dissected intestines.

It is possible to track T-cells in vivo by bioluminescence imaging (BLI) with a firefly Luciferase that has been optimized for in vivo use (FIG. 7). In this experiment, BLI signal decay and weight is compared over 7 days. Following this, mice are sacrificed. Persistence of donor T-cells is measured by quantitative flow cytometry from blood, bone-marrow and spleen. GvHD is measured by histological assessment of intestine and liver.

Figure 15:
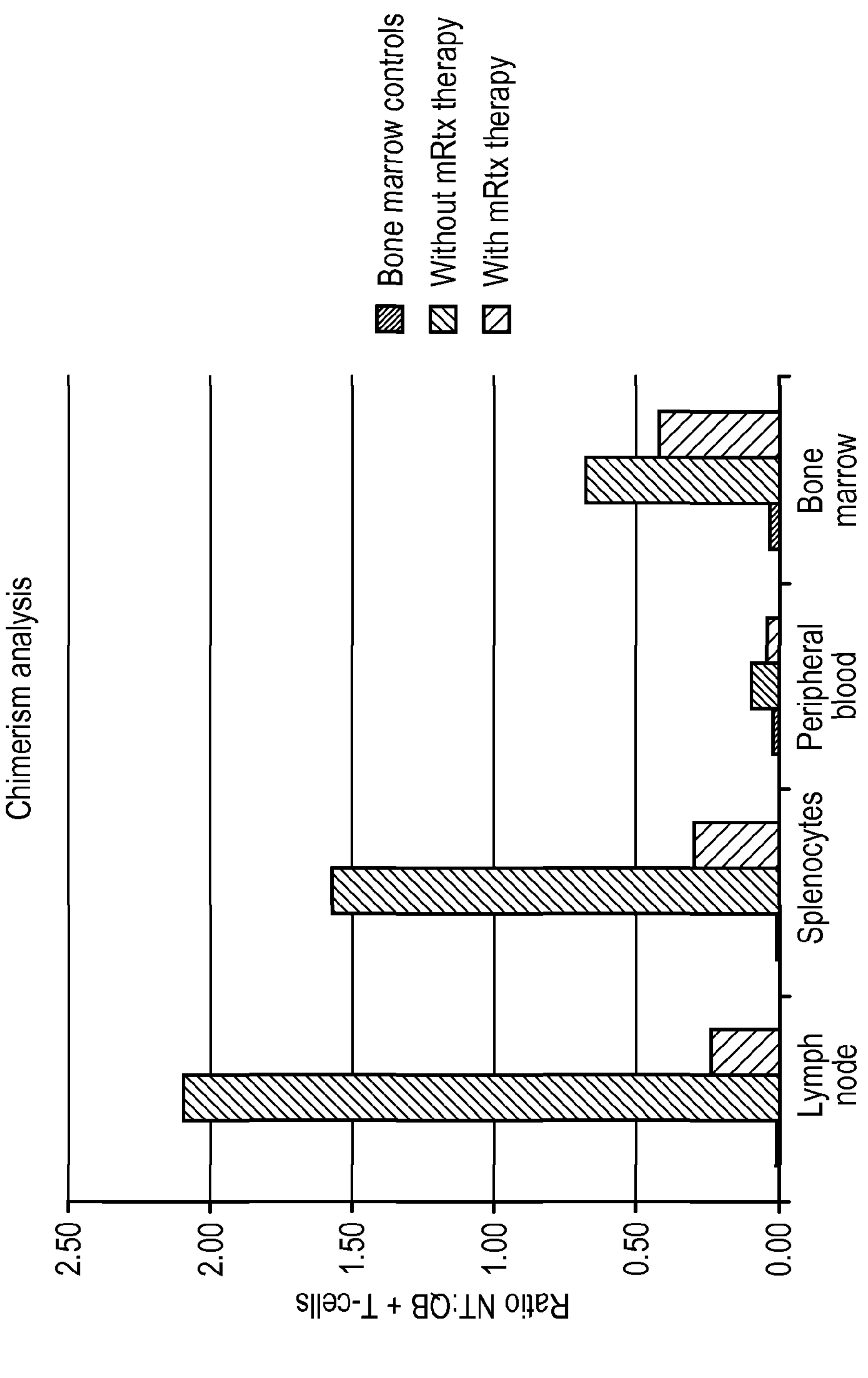
FIG. 15. GvHD model assessment
Figure 16:
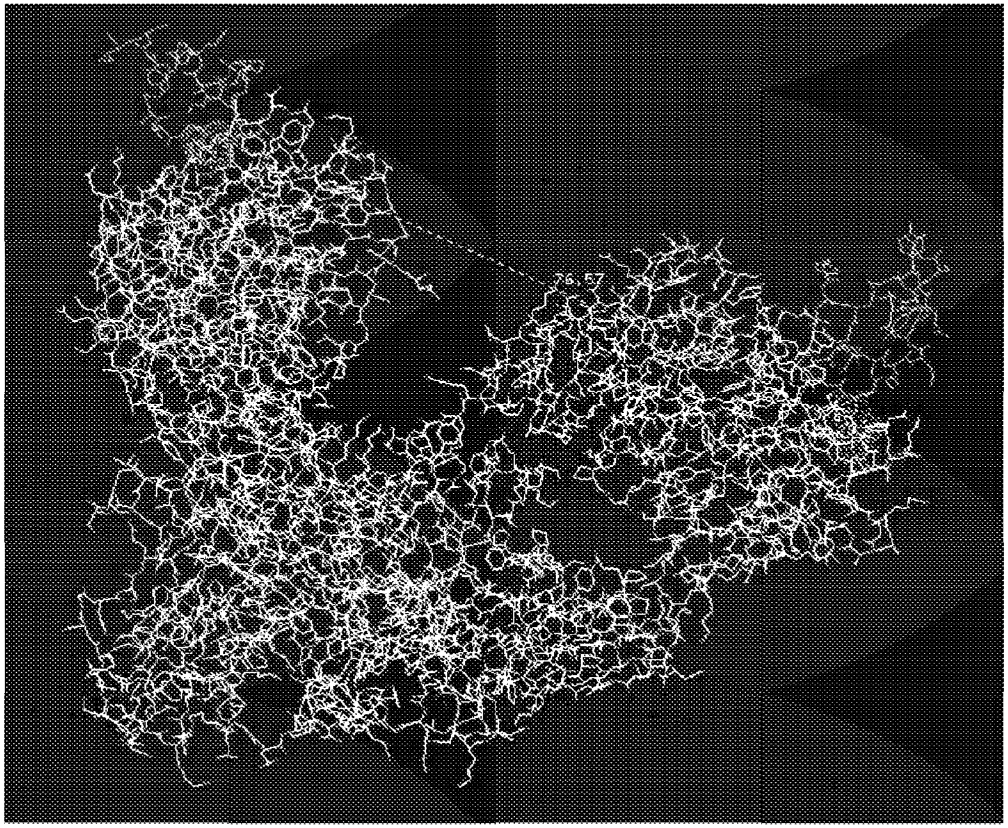
FIG. 16. Schematic diagram showing crystal structure and approximate distance
Figure 16:
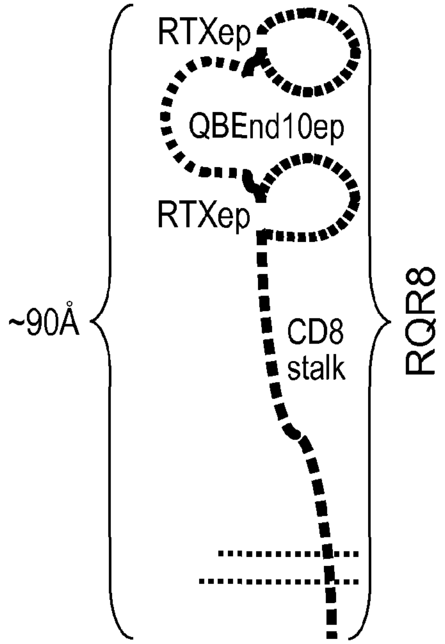

As shown in FIG. 15, there is a clear benefit for mice receiving RQR8 as illustrated by survival and GvHD resolution. Bone marrow appears to be the donor cell reservoir. The data illustrated by this image represents the residual engraftment of transgenic cells in the recipient mice following murine Rituximab-mediated deletion. The height of the bars indicates the proportional level of engrafted T-cells as a proportion of the T-cell compartment in the mouse at the end of the experiment. Clearly the red bars are considerably higher than the green bars demonstrating the level of engraftment of transgenic cells in the absence of Rituximab-mediated deletion.

In order to compare iCasp9 and HSV-TK with RQR8, splenocytes transduced with constructs (b'), (c) and (d') are administered to transplanted mice. At day 10, ritux-mG2a, AP20187 and Ganciclovir are administered respectively. BLI signal decay over time and weight loss are measured followed by quantification of persistence of donor T-cells and GvHD by histology on sacrifice at day 17.

CONCLUSIONS

The present inventors have created a 136 amino acid marker/suicide gene for T-cells. The translated protein is stably expressed on the cell surface after retroviral transduction. It binds QBEND10 with equal affinity to full length CD34. Further, the construct binds Rituximab, and the dual epitope design engenders highly effect complement mediated killing. Due to the small size of the construct, it can easily be co-expressed with typical T-cell engineering transgenes such as T-cell receptors or Chimeric Antigen Receptors and others allowing facile detection, cell selection as well as deletion of cells in the face of unacceptable toxicity with off the shelf clinical-grade reagents/pharmaceuticals.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cell therapy, T-cell engineering, molecular biology or related fields are intended to be within the scope of the following claims.

The invention claimed is:

1. A polypeptide having the formula:

St-R1-S1-Q-S2-R2 wherein

R1 and R2 are a Rituximab-binding epitopes each having an amino acid sequence selected from the group consisting of SEQ ID NOs: 1, 6, 7, 8, 9, 10, 11, 12, 13, 14, 15 and 16;

S1 and S2 are spacer sequences, which may be the same or different;

Q is a QBEnd10-binding epitope having the amino acid sequence shown as SEQ ID NO: 2;

St is a stalk sequence which, when the polypeptide is expressed at the surface of a target cell, causes the R and Q epitopes to be projected from the cell surface; and wherein the spacer sequences S1 and S2 have a combined length of at least about 10 amino acids, such that the distance between R1 and R2 is too long for the polypeptide to bind both antigen binding sites of Rituximab simultaneously.

2. A polypeptide according to claim 1, wherein the distance between R1 and R2 is more than 76.57 Å.

3. A polypeptide according to claim 1, wherein the stalk sequence is derivable from CD8alpha.

4. A polypeptide according to claim 1 which comprises the sequence shown as SEQ ID NO: 4.

5. A vector which comprises a nucleic acid sequence encoding a polypeptide having the formula:

St-R1-S1-Q-S2-R2 wherein

R1 and R2 are a Rituximab-binding epitopes each having an amino acid sequence selected from the group consisting of SEQ ID NOs: 1, 6, 7, 8, 9, 10, 11, 12, 13, 14, 15 and 16;

S1 and S2 are spacer sequences, which may be the same or different;

Q is a QBEnd10-binding epitope having the amino acid sequence shown as SEQ ID NO: 2;

St is a stalk sequence which, when the polypeptide is expressed at the surface of a target cell, causes the R and Q epitopes to be projected from the cell surface; and wherein the spacer sequences S1 and S2 have a combined length of at least about 10 amino acids, such that the distance between R1 and R2 is too long for the polypeptide to bind both antigen binding sites of Rituximab simultaneously.

6. A vector according to claim 5, which also comprises a transgene of interest.

7. A vector according to claim 6, wherein the transgene of interest encodes a chimeric antigen receptor or a T-cell receptor, such that when the vector is used to transduce a target cell, the target cell co-expresses the polypeptide and the chimeric antigen receptor or T-cell receptor.

8. A cell which expresses a polypeptide according to claim 1.

9. A cell according to claim 8 which co-expresses the polypeptide and a protein of interest (POI) at the cell surface.

10. A cell which comprises a nucleic acid sequence encoding a polypeptide having the formula:

St-R1-S1-Q-S2-R2 wherein

R1 and R2 are a Rituximab-binding epitopes each having an amino acid sequence selected from the group consisting of SEQ ID NOs: 1, 6, 7, 8, 9, 10, 11, 12, 13, 14, 15 and 16;

S1 and S2 are spacer sequences, which may be the same or different;

Q is a QBEnd10-binding epitope having the amino acid sequence shown as SEQ ID NO: 2;

St is a stalk sequence which, when the polypeptide is expressed at the surface of a target cell, causes the R and Q epitopes to be projected from the cell surface; and wherein the spacer sequences S1 and S2 have a combined length of at least about 10 amino acids, such that the distance between R1 and R2 is too long for the polypeptide to bind both antigen binding sites of Rituximab simultaneously.

11. A cell according to claim 8, which is a T cell.

12. A polypeptide according to claim 3, wherein the stalk sequence comprises the amino acid sequence shown in SEQ ID NO: 3.

* * * * *